US010130278B2

(12) United States Patent
Jordan et al.

(10) Patent No.: US 10,130,278 B2
(45) Date of Patent: Nov. 20, 2018

(54) WIRELESS EEG UNIT

(71) Applicant: Jordan Neuroscience, Inc., Redlands, CA (US)

(72) Inventors: Kenneth George Jordan, Irvine, CA (US); Gary Loubert, Kanata (CA); David Bakkom, Cedar Grove, WI (US)

(73) Assignee: JORDAN NEUROSCIENCE, INC., Redlands, CA (US)

( * ) Notice: Subject to any disclaimer, the term of this patent is extended or adjusted under 35 U.S.C. 154(b) by 615 days.

(21) Appl. No.: 14/435,728

(22) PCT Filed: Oct. 15, 2013

(86) PCT No.: PCT/US2013/065138
§ 371 (c)(1),
(2) Date: Apr. 14, 2015

(87) PCT Pub. No.: WO2014/062738
PCT Pub. Date: Apr. 24, 2014

(65) Prior Publication Data
US 2015/0257674 A1    Sep. 17, 2015

Related U.S. Application Data

(60) Provisional application No. 61/713,754, filed on Oct. 15, 2012.

(51) Int. Cl.
*A61B 5/04*        (2006.01)
*A61B 5/0478*      (2006.01)
(Continued)

(52) U.S. Cl.
CPC .......... *A61B 5/0478* (2013.01); *A61B 5/0006* (2013.01); *A61B 5/04012* (2013.01);
(Continued)

(58) Field of Classification Search
CPC ............... A61B 5/0478; A61B 5/0006; A61B 5/04012; A61B 5/6803; A61B 6/032; A61B 6/4417; A61B 6/501

See application file for complete search history.

(56) References Cited

U.S. PATENT DOCUMENTS 3,978,847 A  * 9/1976  Fehmi ................. A61B 5/0424
                                                      600/545
6,383,143 B1    5/2002  Rost
(Continued)

FOREIGN PATENT DOCUMENTS

| DE | 10 2010 005551 | 7/2011 |
| WO | 1982/003977 | 11/1982 |
| WO | 2008/092098 | 7/2008 |

OTHER PUBLICATIONS

International Search Report and Written Opinion, International Patent Application No. PCT/US2013/065138, dated Jan. 30, 2014.
(Continued)

*Primary Examiner* — Mallika D Fairchild
(74) *Attorney, Agent, or Firm* — Loza & Loza, LLP; Michael F. Fedrick

(57) ABSTRACT

A device for performing EEG which consists of an elastic head strap, electrodes, and a wireless transmitter. The wireless transmitter, which displays indicators of electrode impedance, is secured to a patient using a docking station attached to the head strap at the crown of a subject's head and is placed into electrical communication with the electrodes using conductive thread sewn into the head strap. A simplified user interface comprising graphical elements improves the detection of brain wave patterns.

19 Claims, 26 Drawing Sheets

(51) Int. Cl.
*A61B 5/00* (2006.01)
*A61B 6/03* (2006.01)
*A61B 6/00* (2006.01)

(52) U.S. Cl.
CPC ............ *A61B 5/6803* (2013.01); *A61B 6/032* (2013.01); *A61B 6/4417* (2013.01); *A61B 6/501* (2013.01)

(56) References Cited

U.S. PATENT DOCUMENTS

| | | | |
|---|---|---|---|
| 6,708,051 | B1 | 3/2004 | Durousseau |
| 2001/0044573 | A1 | 11/2001 | Manoli |
| 2003/0018278 | A1 | 1/2003 | Jordan |
| 2005/0247319 | A1 | 11/2005 | Berger |
| 2007/0055169 | A1 | 3/2007 | Lee |
| 2007/0255127 | A1 | 11/2007 | Mintz et al. |
| 2009/0259137 | A1* | 10/2009 | Delic .................. A61B 5/0478 600/545 |
| 2009/0281446 | A2 | 11/2009 | Ludving |
| 2011/0130675 | A1 | 6/2011 | Bibian et al. |
| 2012/0234105 | A1 | 4/2012 | Taylor |
| 2012/0143020 | A1 | 6/2012 | Bordoley et al. |
| 2012/0157807 | A1 | 6/2012 | Virtanen |
| 2013/0123585 | A1* | 5/2013 | Kang .................... A61B 5/048 600/301 |

OTHER PUBLICATIONS

International Preliminary Report on Patentability, International Patent Application No. PCT/US2013/065138, dated Apr. 30, 2015.
Tredeks, "Elektroentsefalografy serii 'Ekspert' of Tredeks pa vygodnoy tsene", Dec. 1, 2010 (English language and corresponding Russian language web pages).
Agarwal, Rajeev, "Long-Term EEG Compression for Intensive-Care Settings," IEEE Engineering in Medicine and Biology, Sep./Oct. 2001, pp. 23-29.
Partial supplementary European search report for corresponding European Patent App. No. 13 84 7769, dated Jun. 6, 2016.
Extended European Search Report for corresponding European Patent Application No. 3235426 dated Jan. 23, 2018.

* cited by examiner

WIRELESS EEG UNIT

CROSS-REFERENCE TO RELATED APPLICATIONS

This application is the U.S. national stage of International Patent Application No. PCT/US2013/065138, filed on Oct. 15, 2013 and entitled WIRELESS EEG UNIT, which claims the benefit of priority under 35 U.S.C. § 120 from U.S. Patent Application No. 61/713,754, filed Oct. 15, 2012. The disclosures of the foregoing applications are incorporated herein by reference in their entirety.

BACKGROUND

Electrical potentials are generated by ionic current flows within the neurons of the brain. Such current flows can be detected by electroencephalography (EEG). EEG devices record the brain's electrical activity and display it in the form of an electroencephalogram (EEG), which generally depicts waveforms of varying frequency and amplitude as measured in voltage. EEG waveforms are generally classified according to their frequency (standard frequency ranges termed alpha, beta, theta, and delta), amplitude, and shape, as well as by the sites on the scalp at which they are recorded.

An irregular brain wave pattern can be indicative of a particular brain pathology. Distinctive EEG patterns are seen, for example, in acquired brain injury (ABI), accelerated cerebral edema, expanding intracranial masses, and severe cerebral ischemia. Such patterns include encephalographic seizures, markedly slow frequencies, amplitude suppression, "burst suppression," and periodic epileptiform discharges (PEDS) (Jordan 2004, Khan et al 2005, Schneider 2005). While not specific for particular diagnoses, these patterns provide an early, sensitive and reliable warning of severe or worsening brain damage.

The use of EEG when brain injury is suspected is of particular importance because EEG can detect injuries at an early stage, before they progress to more serious conditions. For example, in moderate to severe traumatic ABI, such as from the blast of an explosion or a concussive impact, or in non-traumatic ABI from a stroke or hemorrhage, death or irreversible brain injury are most closely associated with "secondary progression" events that can be detected with EEG, including brain edema, enlarging hemorrhages, seizures, torn or occluded blood vessels, and brain herniation. In the context of acute traumatic brain injury (ATBI), EEG can provide an early warning of worsening brain damage and provide clues about the underlying disease process.

Conventional continuous EEG (CEEG) methods have changed little in decades, and are both inefficient and labor intensive. EEG is oftentimes not readily available, even in hospitals, and delays of hours may occur before an EEG procedure is performed and the results interpreted. Such delays can result in a patient not receiving appropriate treatment, resulting in preventable and sometimes irreversible harm to the patient. The complexity and time involved in applying electrodes to a patient's scalp using traditional EEG can contribute to such delays, as can the absence of a physician or a technician trained to interpret EEG results in a hospital.

There remains a need, therefore, for real-time, functional brain state assessment technology which can be performed in a variety of settings where it may be needed, for example in sports venues, emergency response situations, and battlefield settings.

SUMMARY

The present invention comprises a wireless EEG device that includes:
  (a) a head strap for retaining a plurality of electrodes on the head of a subject, the head strap comprising at least a sagittal strap portion;
  (b) a docking station attached to the sagittal strap portion at the crown of the subject's head, the docking station comprising:
    a base formed from a material which is transparent to X-rays,
    a receptacle supported by the base, and, optionally
    a cover placed over the wireless transmitter; and
  (c) a wireless transmitter in electrical communication with the plurality of electrodes for transmitting an electrical signal received by the electrodes from the subject's brain which is securely retained within the receptacle.

The base of the docking station is preferably formed from a foam material having a thickness of at least 1.3 centimeters, more preferably of between 2.5 and 6 centimeters. The base and receptacle can be integrally formed, preferably from a material that absorbs, scatters and/or reflects less than 20% of X-ray radiation received by the base and the receptacle, more preferably less than 10%, and even more preferably less than 1%. The plurality of electrodes, which can be needle electrodes, disc electrodes, and/or cup electrodes, are preferably placed in electrical communication with the wireless transmitter using non-ferromagnetic electrically conductive thread. The wireless EEG device can be used to perform EEG, and a CT scan or X-ray image can be further obtained without removing the strap and docking station from a subject's head.

In another embodiment, the present invention comprises an EEG device that includes:
  (a) a head strap formed from an elastic material, the head strap comprising a plurality of head strap portions which extend across a plurality of EEG electrode positions on the head of a subject, the electrode positions being selected from the group consisting of Fp1, Fp2, F7, F3, Fz, F4, F8, A1, T3, Cz, C3, C4, T4, A2, T5, P3, Pz, P4, T6, O1, and O2;
  (b) a plurality of electrodes attached to the head strap at the plurality of EEG electrode positions;
  (c) a plurality of non-ferromagnetic electrically conductive threads, which can comprise copper or silver, each conductive thread being in electrical communication at a first end with one of the plurality of electrodes and at a second end with an electrical connector that can be further connected to a transmitter.

The conductive thread is preferably secured to the head strap by passing the conductive thread from an upper surface of the head strap to a lower surface and then from the lower surface to the upper surface in a repetitive manner along a longitudinal extent, thereby disposing the conductive thread in a sinuously curved manner along the extent of the head strap, in the manner of sewing. Each of the conductive threads preferably have a diameter of between 0.5 millimeters (mm) and 5 mm, and more preferably between 2 mm and 4 mm. At least a portion of one or more of the conductive threads are also preferably disposed in stitches having a length of between 0.5 mm and 10 mm, more preferably between 1 mm and 5 mm, and even more preferably between 2.5 mm and 3.5 mm. In addition, the conductive threads are each preferably surrounded by an electrically insulating material.

The transmitters used in the present invention are adapted for use with an EEG device and can include:
(a) a communications interface comprising an electrode interface communicatively coupled to a plurality of electrodes;
(b) a user interface including at least one electrode impedance indicator; and
(c) a processing circuit coupled with the communications interface and the user interface, the processing circuit adapted to:
receive a respective electrical signal from each of the plurality of electrodes;
measure an impedance associated with each electrode of the plurality of electrodes; and
visually display via the at least one electrode impedance indicator whether the impedance associated with each electrode is above or below a predetermined threshold.

In these transmitters, the communications interface can further comprise a wireless transceiver, and the processing circuit can be adapted to simultaneously transmit via the wireless transceiver the impedance associated with each electrode and an electrical signal received by each electrode from a subject's brain.

In an alternative embodiment, the transmitters used in the present invention can include:
(a) a communications interface comprising:
a wireless transceiver; and
an electrode interface communicatively coupled to a plurality of electrodes; and
(b) a processing circuit coupled with the communications interface and the user interface, the processing circuit adapted to:
measure an impedance associated with each electrode of the plurality of electrodes;
receive via the electrode interface a respective electrical signal by each electrode from a subject's brain; and
simultaneously transmit via the wireless transceiver the measured impedance associated with each electrode and the respective electrical signal by each electrode from a subject's brain.

The present invention also includes a method of evaluating the brain activity of a subject using an EEG. In this method, an EEG comprising waveforms generated by electrical activity within each of the two hemispheres of the brain of the subject is obtained. Such waveforms occur in predetermined patterns, and can be displayed as visually distinguishable indicia, such as indicia in different colors, in temporal order and in a linear fashion, thereby forming a temporal waveform record in graphical form. EEG data from the EEG is preferably processed in predetermined time segments, the time segments preferably being between 5 seconds and 20 seconds in length, and advantageously being 10 seconds in length. The waveform patterns for each hemisphere of the subject's brain are also preferably displayed separately. The predetermined indicia indicates a predetermined waveform pattern, such as suppression, slowing, burst-suppression, inter-hemisphere asymmetry, periodic epileptiform discharge, or seizure.

The method further includes playing a time indicator in the temporal waveform record, the time indicator designating a time point in the temporal waveform record. Preferably, waveform patterns of both hemispheres of the subject's brain are displayed together in parallel. A graphical image having two adjacent predetermined display areas is then displayed. The indicia displayed in each display area correspond to the indicia in the temporal waveform record for a respective hemisphere of the subject's brain at the point in the temporal waveform record where the time indicator is displayed.

FIGURES

FIG. 16 is a top plan view of the transmitter of FIG. 15 showing a power indicator and impedance indicators powered on.

DESCRIPTION

Definitions

Figure 1:
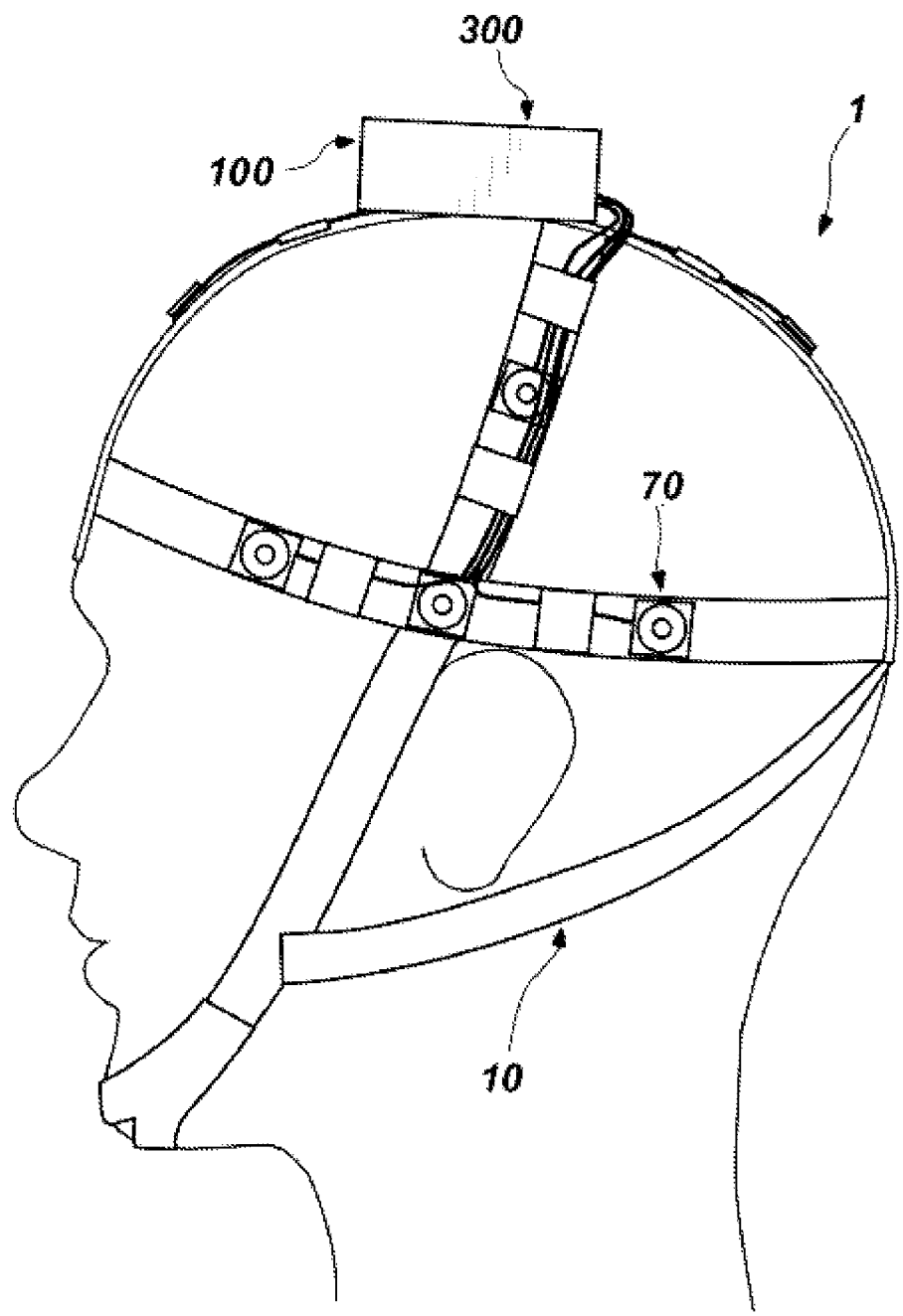
FIG. 1 is a left side elevation view of the present EEG device being worn by a subject.
Figure 2:
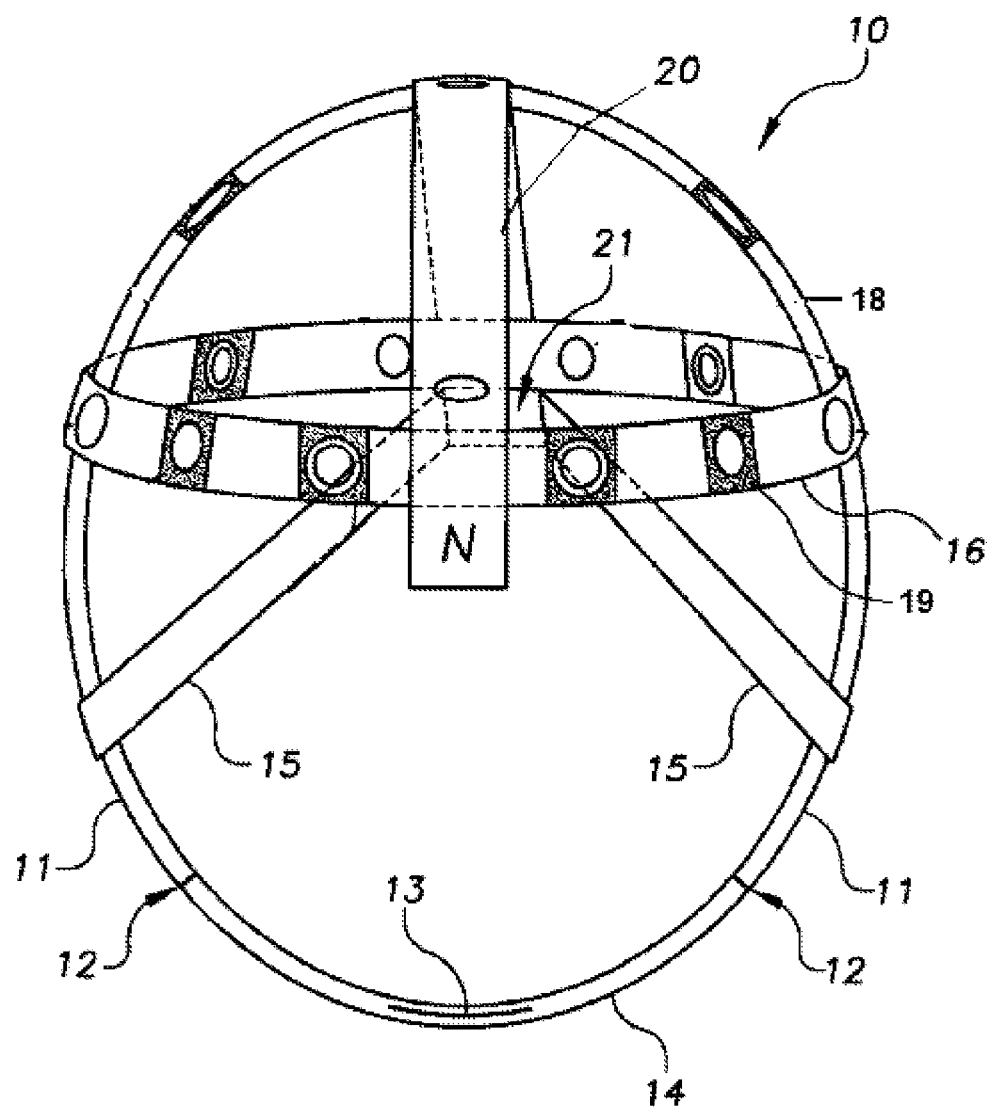
FIG. 2 is a front elevation view of a head strap for use with the present EEG device.

As used herein, the following terms and variations thereof have the meanings given below, unless a different meaning is clearly intended by the context in which such term is used.

"Base" refers to the bottom support of a component or device.

"Cloth" refers to a flexible material formed by weaving, knitting, pressing, or felting natural or synthetic fibers, and includes similar materials formed by polymerization or casting.

"Cloud" refers to a network in which computing resources (hardware and/or software) are delivered as a service over a network such as the internet.

"Coronal" refers to an orientation that is within or parallel to a subject's coronal plane, which is a hypothetical vertical plane that divides a subject's body (or a portion thereof) into ventral (front) and dorsal (back) sections, preferably of approximately equal sizes (by width or volume).

"Crown" refers to the top portion of a subject's head when the subject is standing upright, approximately where the sagittal and coronal planes of the subject intersect.

"CT scan" and "CAT scan" refer to X-ray computed tomography, which is a medical imaging procedure that utilizes computer-processed X-rays to produce tomographic images (generally cross-sectional images) of specific areas of a subject's body.

"Docking station" refers to a hardware frame which provides support and also provides one or more electrical connections.

"EEG" refers to electroencephalography, i.e. the recording of electrical activity at a subject's scalp, in order to measure voltage fluctuations resulting from ionic current flows within the neurons of the subject's brain.

"EEG device" refers to a device for performing EEG.

"Elastic limit," also called the yield point, refers to the stress at which an elastic material ceases to deform elastically and will no longer return to its original shape when the applied stress is removed.

"Ferromagnetic" refers to a characteristic of substances such as iron, nickel, or cobalt and various alloys that are able to form permanent magnets (i.e., they remain magnetized after an external field is removed) under the conditions in which the present invention is used. "Non-ferromagnetic" refers to materials which are not ferromagnetic.

"Impedance" refers to the opposition to flow of alternating current through a circuit.

"Jack" refers to an electrical connector comprising a "female" electrical contact or socket, i.e. which receives another electrical connector, and is generally the more "fixed" connector of a connector pair comprising a jack and a plug.

"Nonconductive" refers to a material which does not conduct electricity under the conditions in which the present device is used.

"Pedestal" refers to a base or supporting structure which supports another component of the present device.

"Plug" refers to an electrical connector comprising a "male" electrical contact or pin, i.e. which is inserted into or onto another electrical connector, and is generally the more movable (less fixed) connector of a connector pair comprising a jack and a plug.

"Programming" refers to instructions, instruction sets, data, code, code segments, program code, programs, subprograms, software modules, applications, software applications, software packages, routines, subroutines, objects, executables, threads of execution, procedures, functions, and similar technology, whether referred to as software, firmware, middleware, microcode, hardware description language, or otherwise.

"Receptacle" refers to a component of the present device having a space of sufficient size and volume to receive some or all of another component or device and thereby retain the other component or device in the receptacle.

"Sagittal" refers to an orientation that is within or parallel to a subject's sagittal plane, i.e. a hypothetical vertical plane which passes from ventral (front) to dorsal (back) of a subject's body, dividing the body into approximately equally sized right and left halves.

"Scalp" refers to the skin covering the head.

"Sew" refers to the attachment of a thread or other length of material to a cloth by passing the thread through one side of the cloth and then back through the other side a plurality of times.

"Strap" refers to a length of flexible material used to secure another component to a particular location.

"Thread" refers to a strand or length of material with a diameter or thickness significantly less than its length, and generally less than 5 millimeters in diameter.

"Transparent" refers to a material which allows a predetermined frequency of electromagnetic radiation to pass through it while absorbing, scattering and/or reflecting less than 20% of the radiation, more preferably less than 10% of such radiation, and even more preferably less than 1%.

"Transverse" refers to an orientation that is within or parallel to a hypothetical horizontal plane that divides a subject's body into superior (upper) and inferior (lower) parts, and is generally perpendicular with respect to the sagittal and/or coronal planes of the subject.

"Visually coded" refers to the use of a predetermined set of visually distinguishable indicia or signals (i.e., two or more visually distinguishable colors, patterns, shadings, and/or other visual referents). Visually coded displays allow a user to distinguish between a first visual signal and a second visual signal on the display, such as one or more areas on a display having a first color and one or more areas having a second color on the display.

"X-ray" refers to a form of electromagnetic radiation having a wavelength in the range of 0.01 to 10 nanometers.

The term "comprise" and variations of the term, such as "comprising" and "comprises," are not intended to exclude other additives, components, integers or steps. The terms "a," "an," and "the" and similar referents used herein are to be construed to cover both the singular and the plural unless their usage in context indicates otherwise.

EEG Device

As shown in FIG. 1, the present EEG device 1 generally comprises a head strap 10 for retaining electrodes 70, a docking station 100, and a wireless EEG transmitter 300. Electrodes 70 are disposed on the head strap 10, and are used to receive electrical signals from the brain of a subject.

Head Strap

As shown in FIGS. 1-9, the head strap 10 can be formed from a plurality of head strap portions. These generally include a transverse strap portion 16, a coronal strap portion 18, and a sagittal strap portion 20. The sagittal strap portion 20 is adapted to be placed approximately within the sagittal plane of the subject's head from a front end on the subject's forehead to a rear end at the back of the subject's head. The coronal strap portion 18 is placed on the subject's head in an orientation that is generally parallel to the coronal plane of the subject's body, although the coronal strap portion 18 or parts of it may deviate from a parallel orientation in order to appropriately place electrodes carried by the coronal strap portion 18, conform to the contours of the subject's head, and better secure the head strap 10. The transverse strap portion 16 is placed on the subject's head in an orientation that is generally parallel to a transverse plane, though deviations to such an orientation likewise occur in order to appropriately place electrodes carried by the coronal strap portion 18 and conform to the contours of the subject's head, as described below. Deviations in the orientation of the strap portion may range from 10°-20° to up to 45°.

The head strap 10 can be secured to a subject in various ways known to the art, such as with fasteners attached to one or both lower ends of jaw straps 11, which can be opposite ends of a strap forming the coronal strap portion 18. In the embodiment shown in FIG. 2, a fastener strap portion 14 of one of the jaw straps 11 attaches to a fastener strap portion 14 of the other jaw strap 11 using a pair of mated connectors, in particular hook and loop fasteners (such as VELCRO brand fastener strips). The fastener strap portion 14 includes a slit 13 through the length of the chin strap 14, in order to better anchor the strap to the patient's chin.

Bias straps 15 can also be added to the head strap 10 to further secure it in place. A preferred construction for the bias straps 15 connects a left bias strap and a right bias strap to a tab 21 of the head strap 10 which extends beyond the transverse strap portion 16. The bias straps 15 are each preferably removably connected to a respective jaw strap 11 with a fastener such as a hook and loop fastener.

Figure 6:
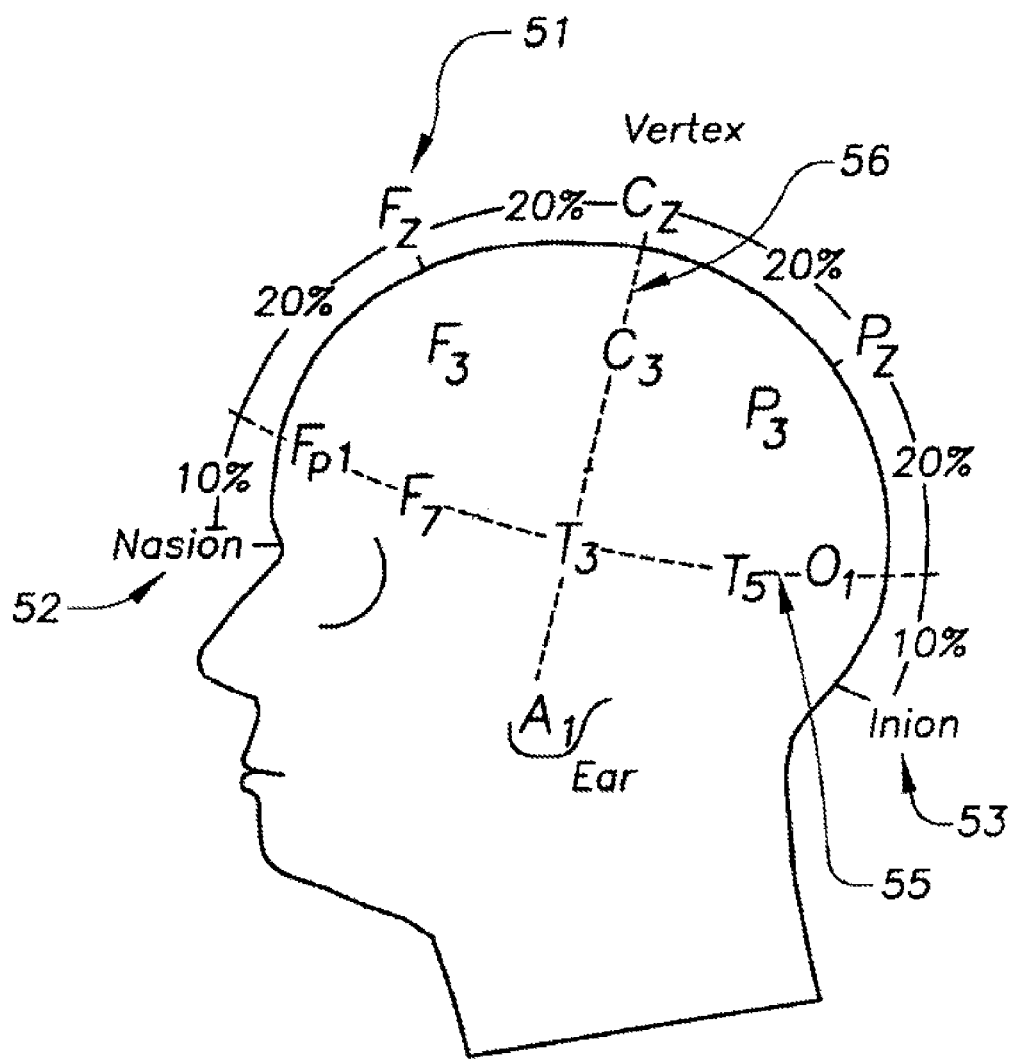
FIG. 6 is a left side elevation view of the positions of electrodes according to the International 10-20 System.
Figure 7:
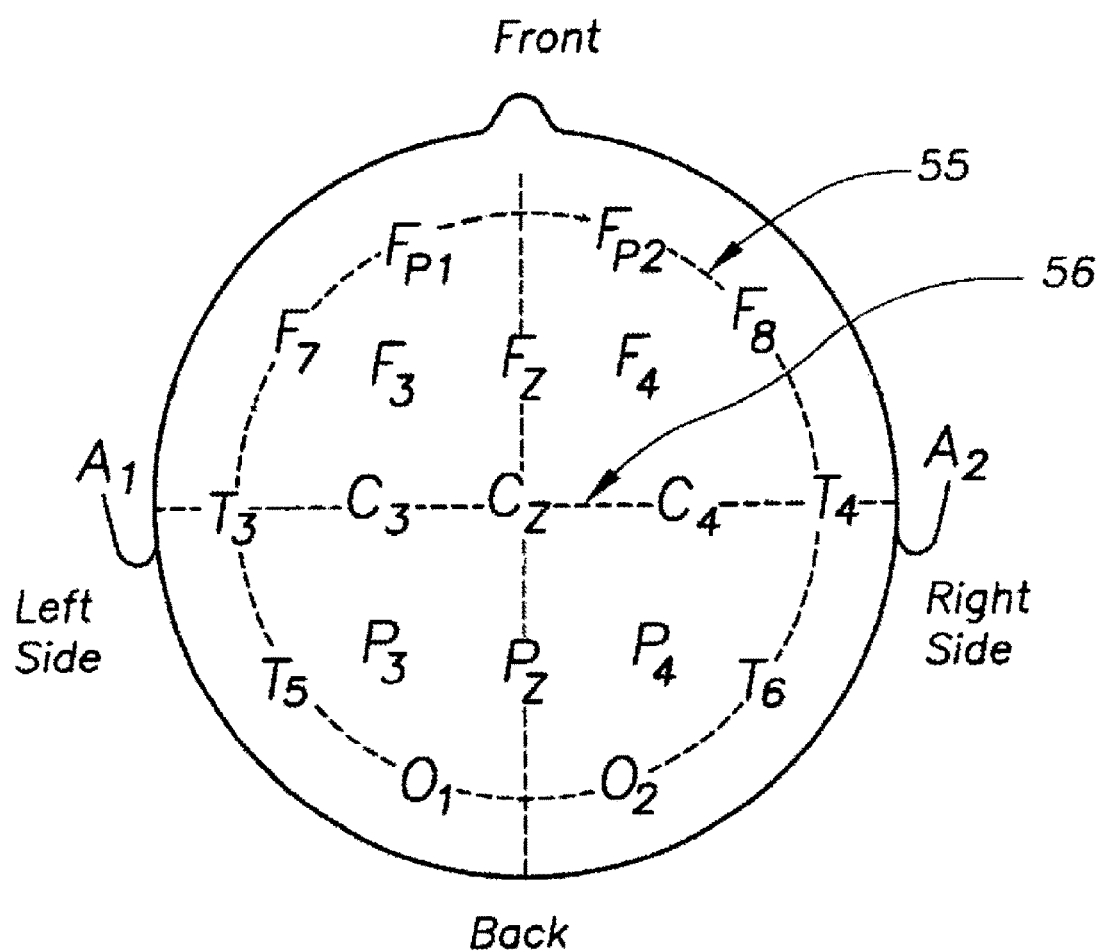
FIG. 7 is a top plan view of the positions of electrodes according to the International 10-20 System.
Figure 8:
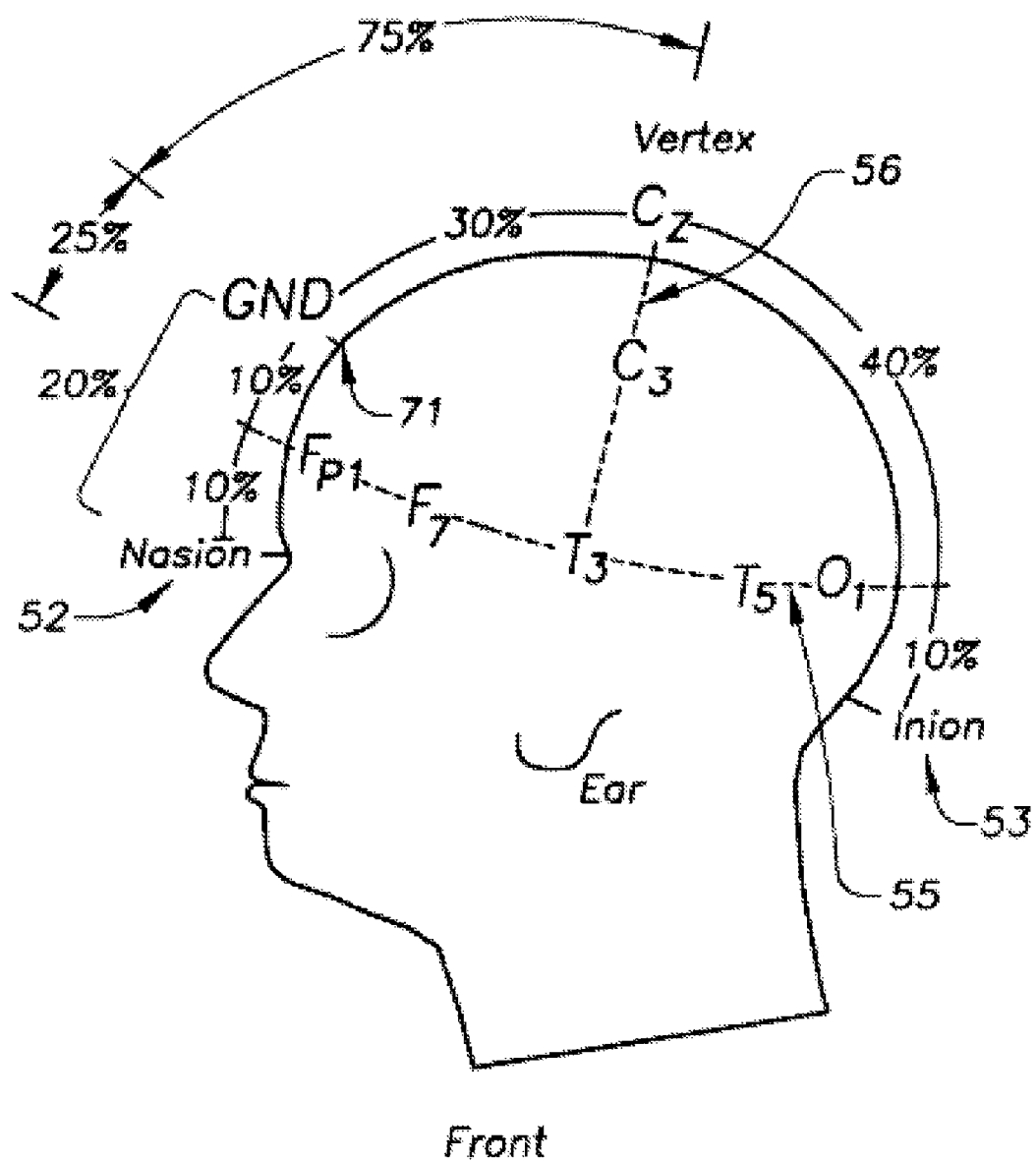
FIG. 8 is a left side elevation view of the positions of electrodes in an alternative embodiment of the present EEG device.
Figure 9:
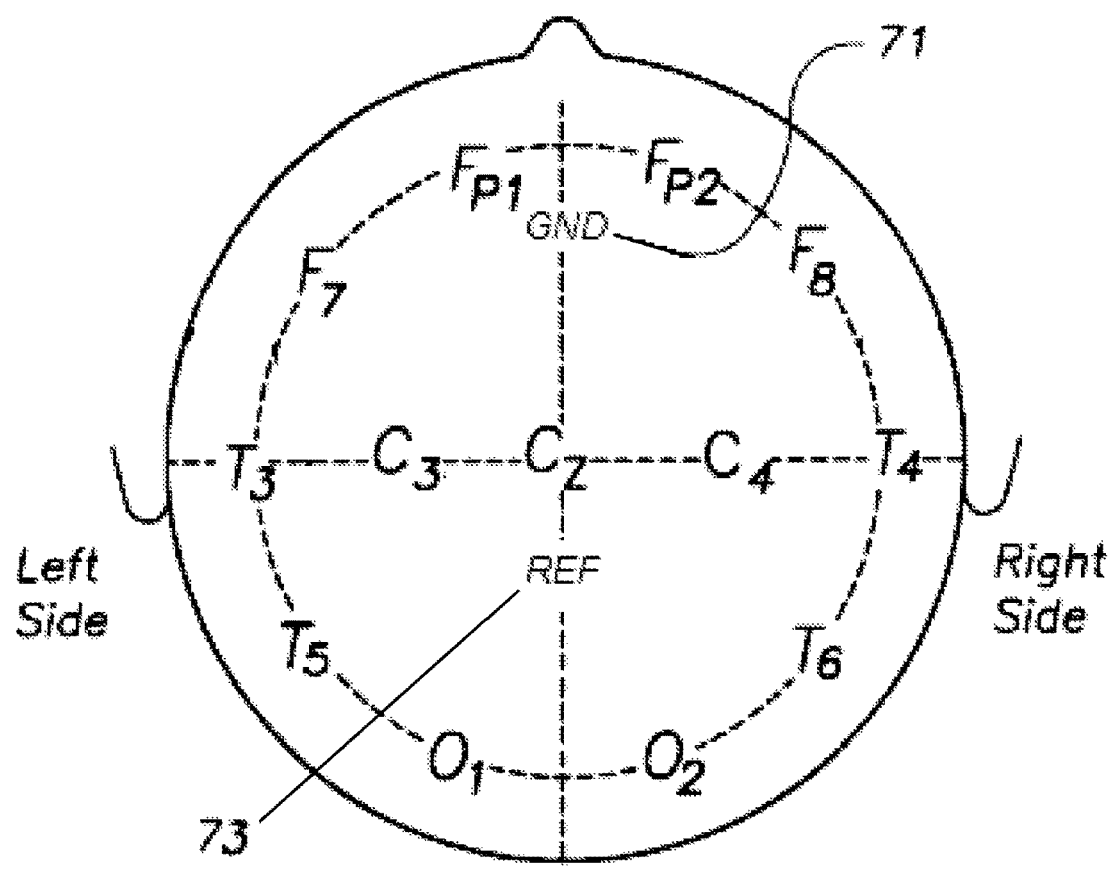
FIG. 9 is a top plan view of the positions of electrodes in the embodiment of FIG. 8.
Figure 10:
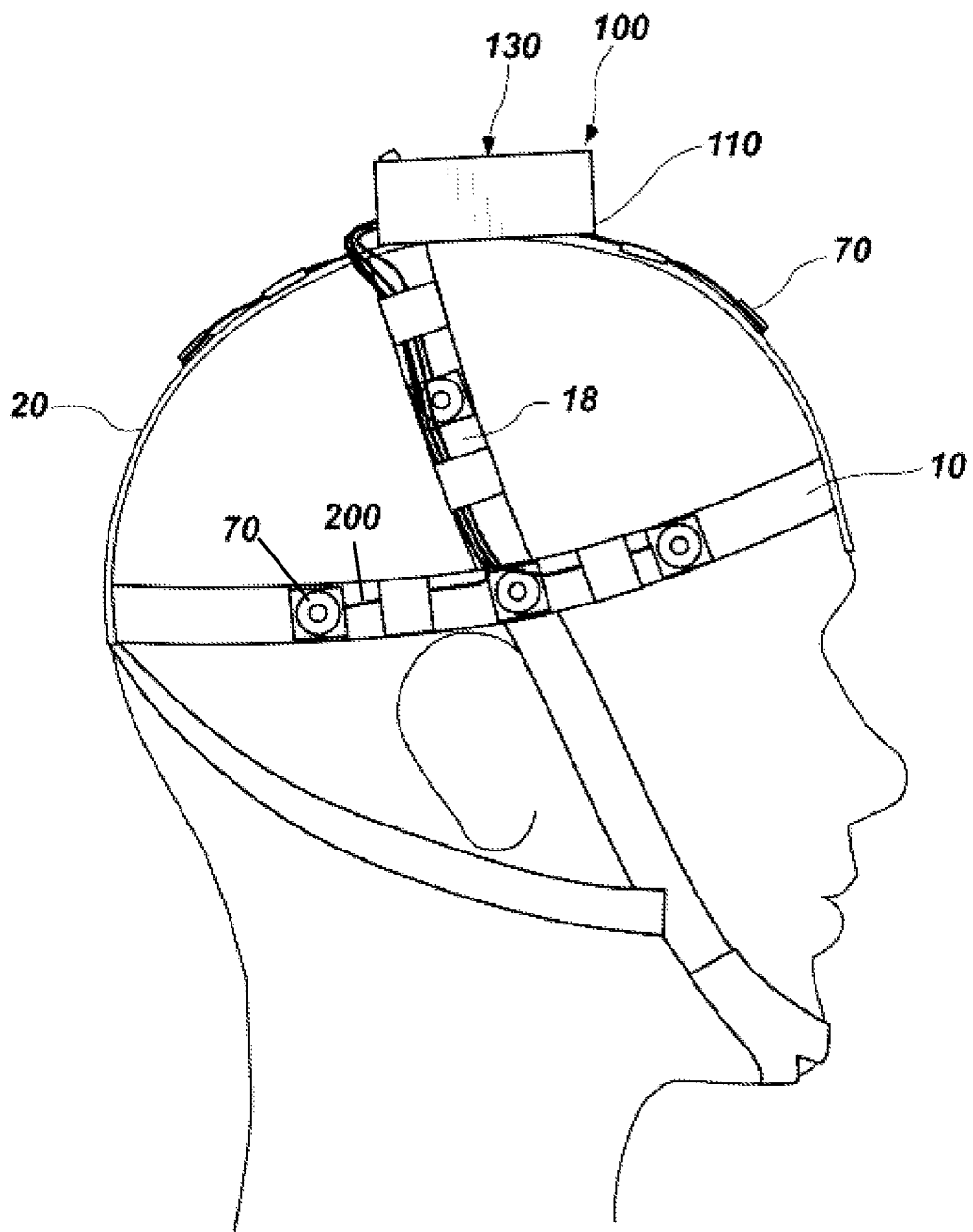
FIG. 10 is a right side elevation view of the docking station of the present EEG device being worn by a subject.
Figure 11:
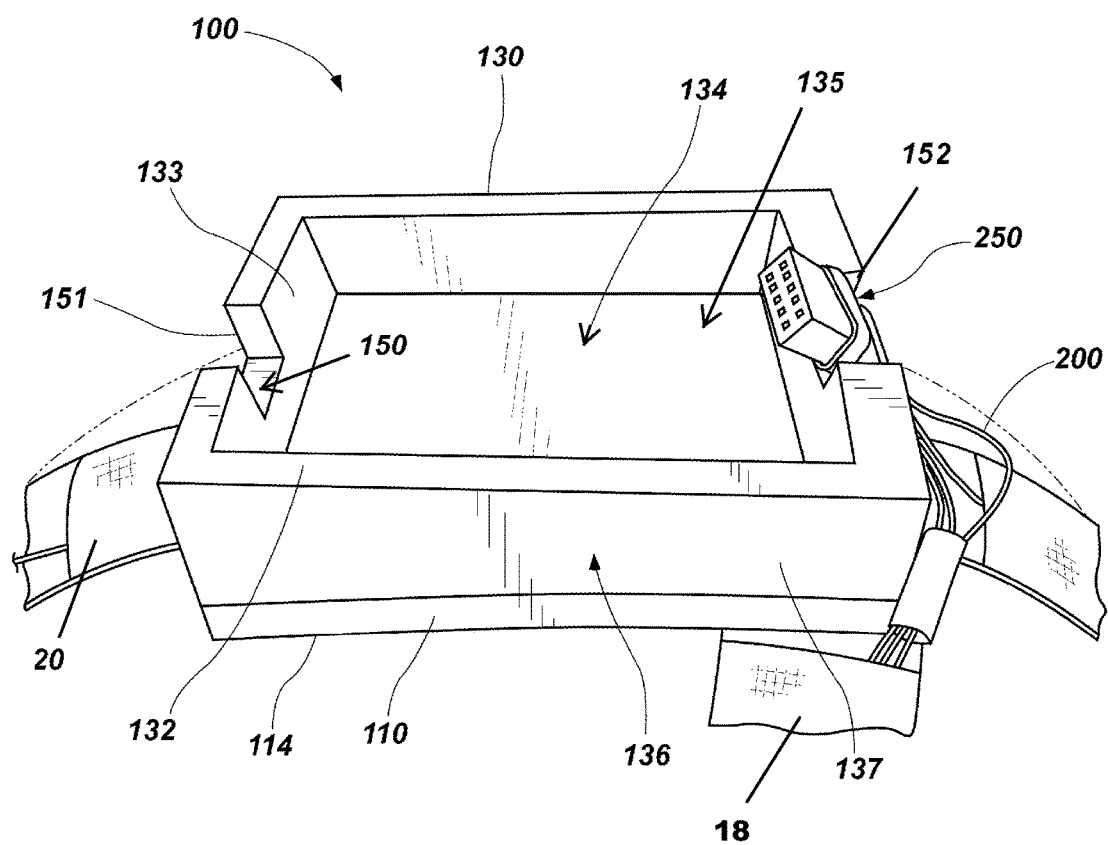
FIG. 11 is a perspective view of the docking station of FIG. 10.
Figure 12:
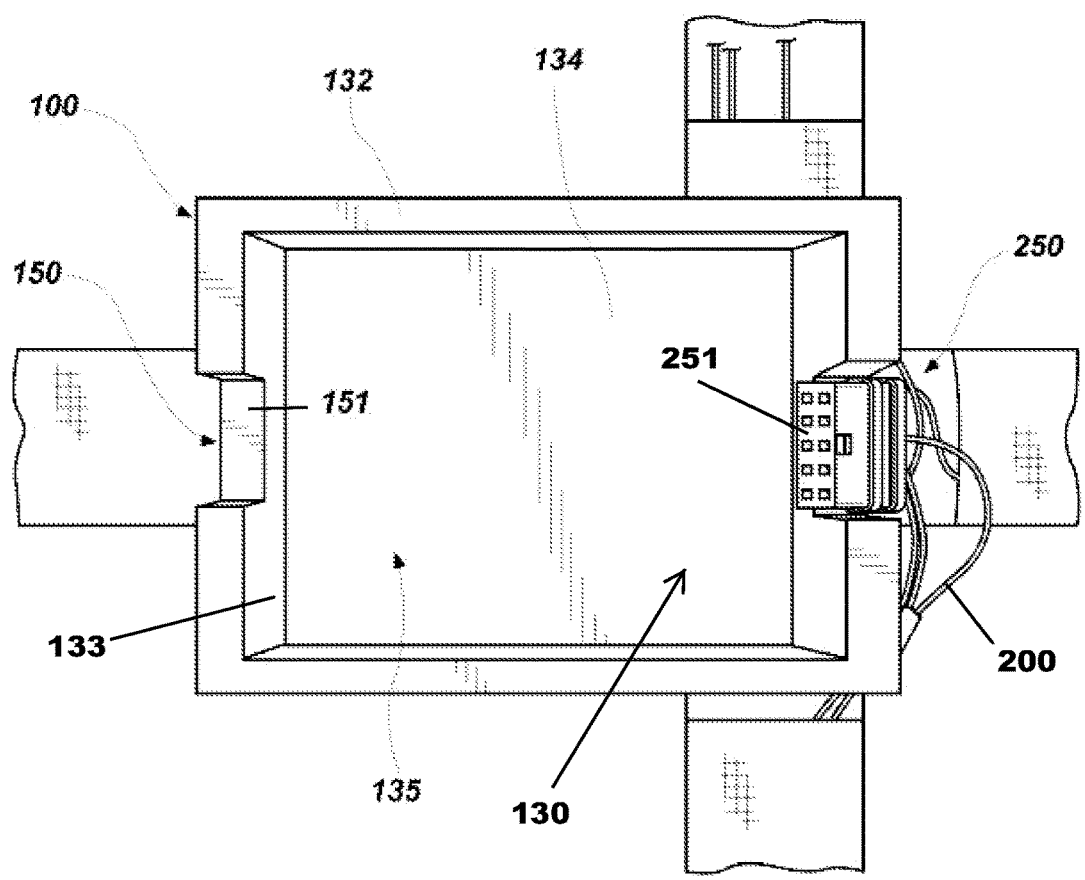
FIG. 12 is a top plan view of the docking station of FIG. 10.
Figure 13:
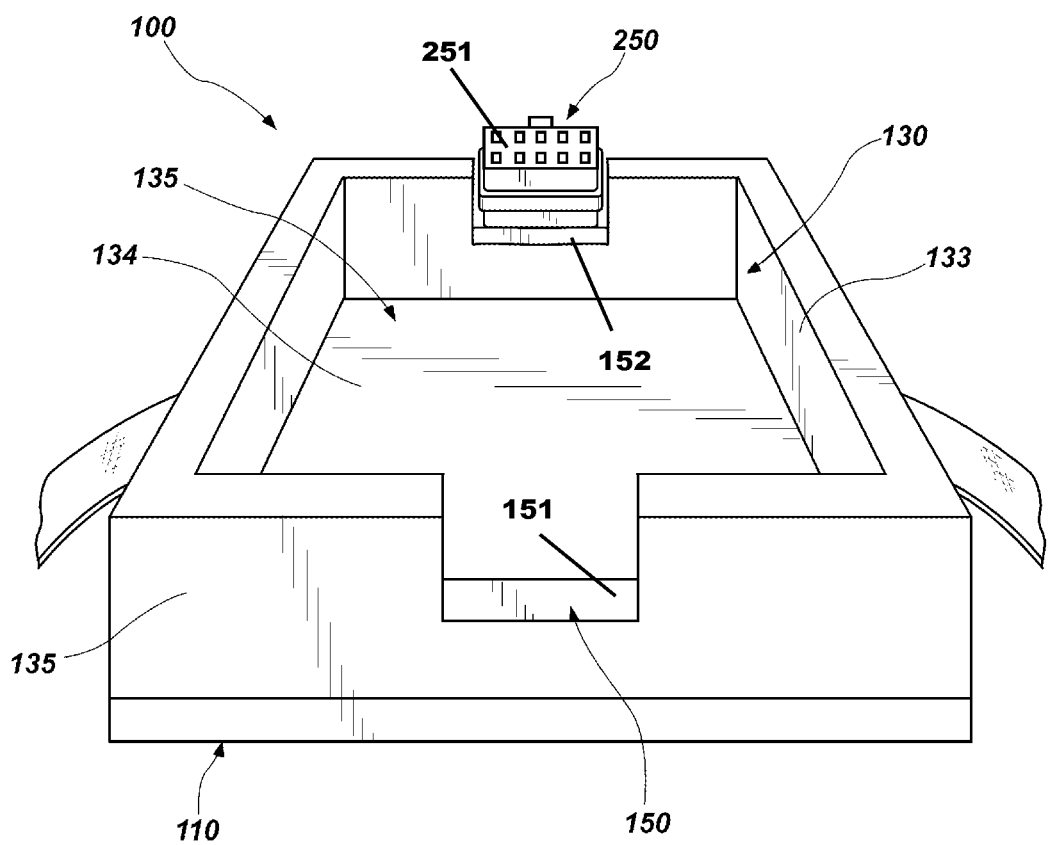
FIG. 13 is front perspective view of the docking station of FIG. 10.
Figure 14:
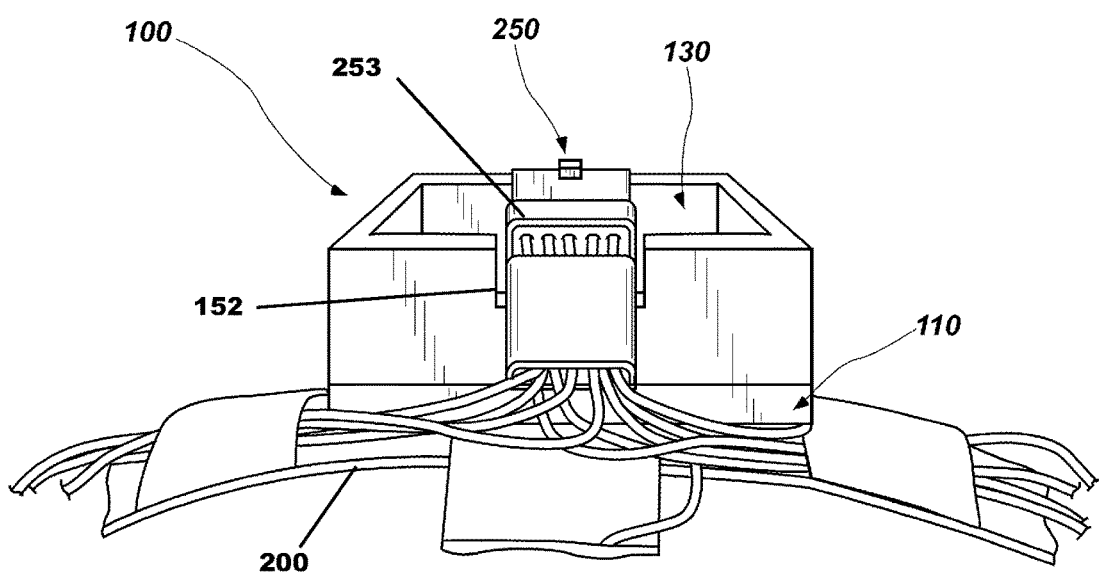
FIG. 14 is a rear elevation view of the docking station of FIG. 10.

The electrodes 70 of the head strap can be placed according to the standard 10-20 electrode placement system for locating EEG electrodes. In the standard 10-20 system, 21 electrodes are placed on a subject's head. These positions are commonly labeled Fp1, Fp2, F7, F3, Fz, F4, F8, A1, T3, Cz, C3, C4, T4, A2, T5, P3, Pz, P4, T6, O1, and O2, and are shown in FIGS. 6 and 7. In an alternative embodiment of the head strap 10 shown in FIGS. 8 and 9, the strap contains no openings for the F3/F4 pair of electrodes or the P3/P4 pair of electrodes, and the openings for the Fz and Pz electrodes are eliminated (electrode locations A1 and A2 frequently generate artifacts and so can also be eliminated when not doing referential recordings). In this embodiment, the head strap 10 has an opening geometry consisting essentially of thirteen openings 19 located according to the International 10-20 System specification for positioning electrodes at points Fp1, Fp2, F7, F8, T3, T4, Cz, C3, C4, T5, T6, O1, and O2, and a fourteenth opening for the ground 71. As shown in FIG. 8, the ground 71 is positioned 25% of the distance from the line 55 which circumscribes the subject's head (approximately in a transverse plane) toward the line 56 which the vertically traverses the subject's head (approximately in a coronal plane), or if measured with reference to the standard skull points of the nasion 52 and inion 53, this location for the ground is approximately 20% of the distance from the nasion 52 to the inion 53. This position of the ground can be varied by approximately half a centimeter in any direction and still achieve the desired result. In addition to the ground 71, which provides grounding of the electrodes to minimize the 60 cycle ambient current interference, a reference electrode (REF) 73 is also preferably provided as a common input for a differential amplifier. In a further alternative, the Fz and Pz electrodes can be included in the head strap 10 in the positions dictated by the standard International 10-20 System.

Figure 3:
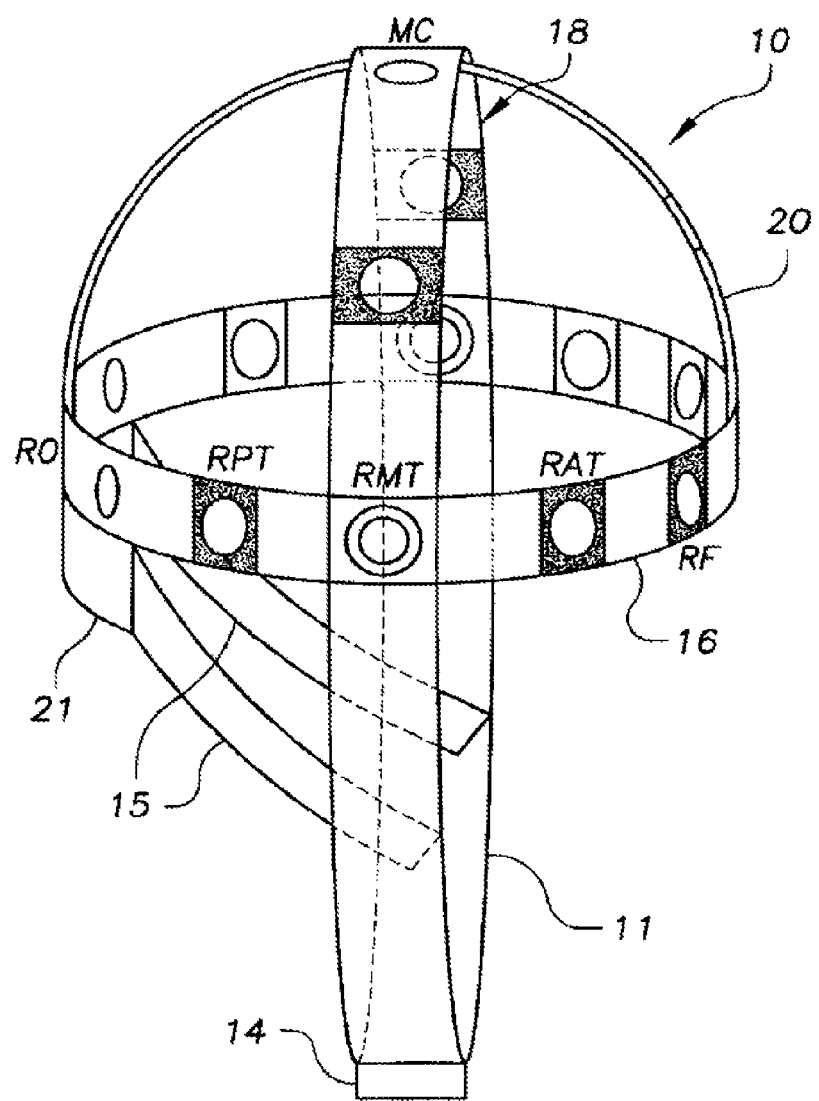
FIG. 3 is the right side elevation view of the head strap of FIG. 2.
Figure 4:
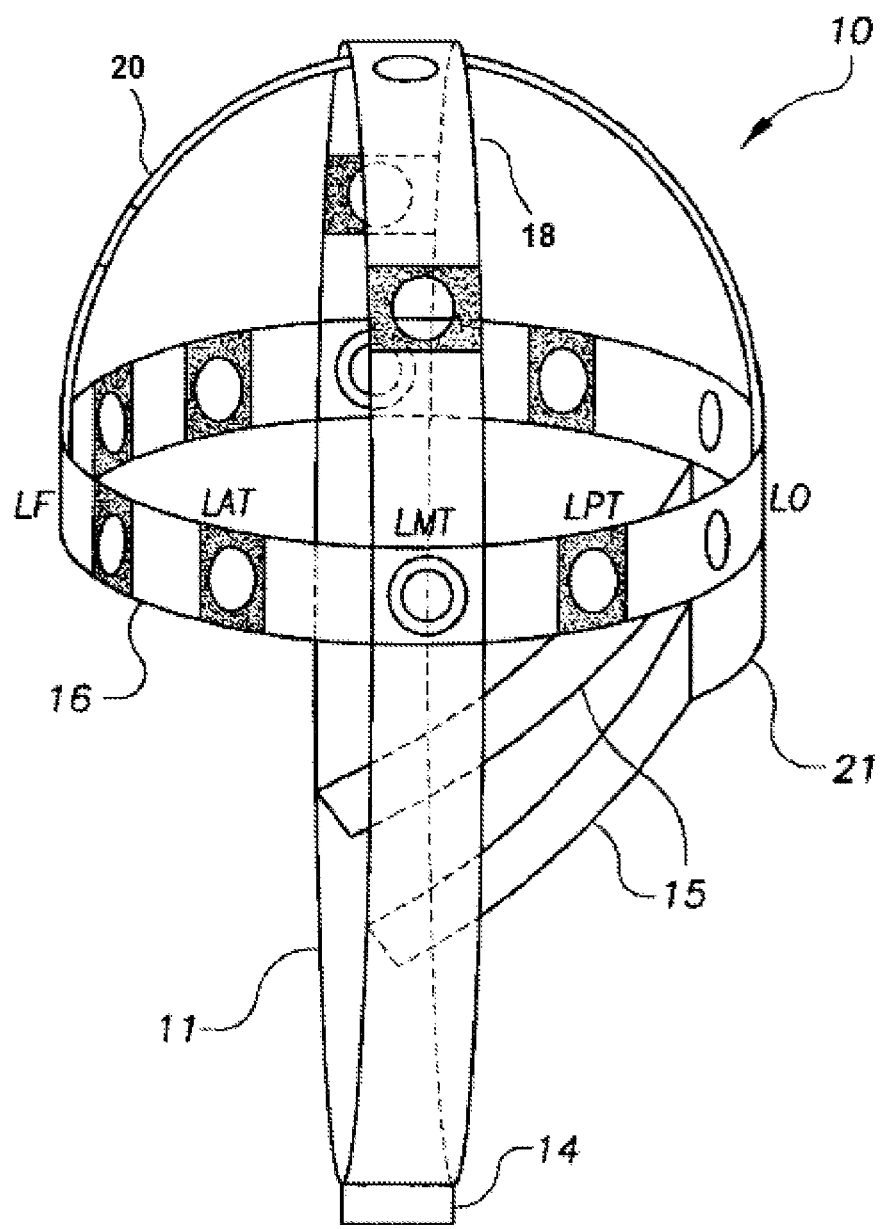
FIG. 4 is the left side elevation view of the head strap of FIG. 2.
Figure 5:
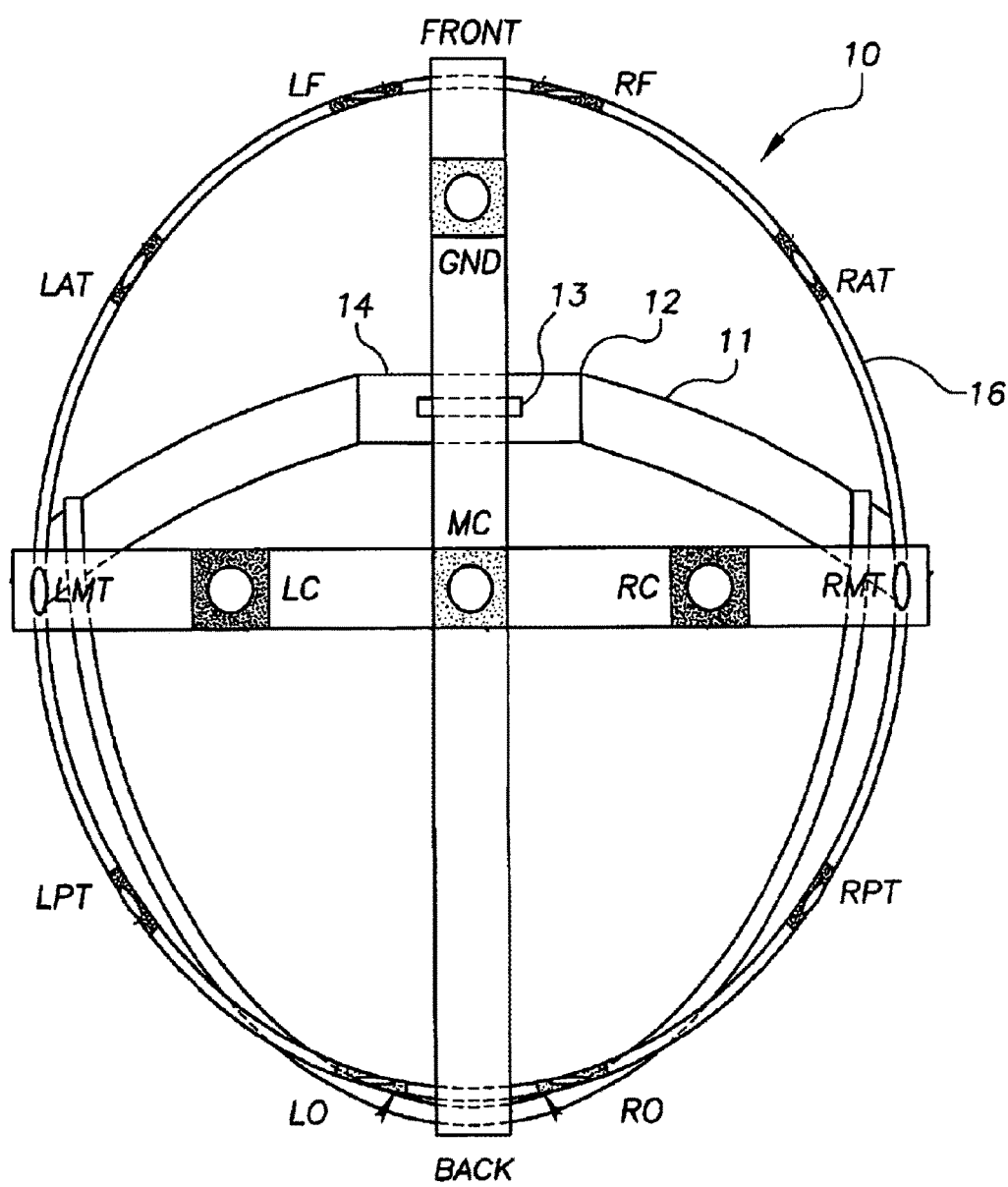
FIG. 5 is a top plan view of the head strap of FIG. 2.

The head strap 10 can be positioned on a subject in any position including supine, sitting, or erect. In a preferred embodiment, the head strap 10 is provided with indicia proximate to the electrode openings 19 in the strap portions in order to guide the placement of the electrodes 70 on the subject's scalp. FIGS. 3-5 include the electrode indicia MC, RC, LC, LO, RO, LPT, RPT, LMT, RMT, LAT, RAT, LF, RF and Gnd, with an "L" prefix being used for left positions and "R" for right positions.

The head strap 10 is preferably made from an elastic material, in particular an elastic cloth, in order to secure the head strap 10 to the head of a subject as well as to secure the electrodes 70 in the proper position. In this case the head strap 10 is preferably sized such that the sagittal strap portion 20 and the transverse strap portion 16, prior to being stretched, have a diameter which is less than the diameter of the head of a subject to be fitted with the head strap 10. The diameter of the subject's head should be within the elastic limit of the material forming the sagittal strap portion 20 and the transverse strap portion 16, so that the head strap 10 can be stretched to fit comfortably over the subject's head and then to contract so as to hold the head strap 10 in a predetermined position by a friction fit.

Electrodes

Any of a variety of electrodes known for use with EEG can be used with the present device 1. For example, the electrodes can be needle electrodes or disc (cup) electrodes. Needle electrodes comprise a needle made of metal or other conductive material, preferably having an impedance of less than 5 ohms. The needle has a pointed end for insertion into the scalp of a subject undergoing EEG and a second end for attachment to a conductive wire, conductive thread, or other electrical connection. Needle electrodes can be attached to a wire or conductive thread directly by soldering, or can be connected by other means, such as to a pin connector which then places the needle into electrical communication with the wire or conductive thread. Exemplative embodiments of needle electrodes can be 7 mm or 13 mm in length, for example. Preferably, a cover is provided for the sharp (pointed) distal end of a needle electrode in order to avoid needle stick injuries.

Needle electrodes have been used in EEG because of their relatively low impedance compared to some other electrode types. They have the disadvantage however of requiring that the subject's skin be pierced by the electrode. Disc electrodes avoid such issues, as they do not require skin abrasion. If the present device is to be used together with MRI imaging, local heating of the needle electrodes may also occur, in which case disc electrodes are preferred.

Disc and cup electrodes can be made from tin, silver, gold, surgical steel, or other electrically conductive materials. They typically have a diameter in the range of 4-10 mm. Disc and cup electrodes can be classified as being either dry electrodes or wet electrodes, depending on the presence of an electrolyte on the surface attached to the skin. Dry electrodes are generally attached to a skin surface mechanically, such as by means of pressure applied by an elastic cloth, as used in the present head strap 10. A wet electrode can be attached to the skin using a conductive liquid, hydrogel or solid gel, e.g. electrolyte gel, to improve the electrical conductivity between the recording (skin) surface and the electrode sensing element. Typical components of a conductive liquid or gel include electrolytes or salts, such as sodium chloride (NaCl) or potassium chloride (KCl), which provide the ionic conductivity.

In one embodiment, a disc electrode for use with the present device 1 can comprise a planar substrate made from a non-conducting material, such as a plastic film, a conductive electrode layer, and an adhesive layer surrounding the conductive electrode layer. The conductive layer can be, for example, silver (Ag), silver/silver chloride (Ag/AgCl), copper (Cu), or carbon (C). An example of a disc electrode for use with the present EEG headgear is a disposable conductive plastic electrode made by Ives EEG Solutions, Inc. (Newburyport, Mass., USA). One advantage of this electrode is that it is compatible with CT scanning. Another exemplary disc electrode is a RINGTRODE electrode (available from Multi Bio Sensors Inc., El Paso, Tex.), comprising a hard plastic disc with a silver/silver chloride (Ag/AgCl) sensor. Disc and cup electrodes can be attached to the head strap 10 by being embedded or sewn into the fabric or other substrate of the head strap, or by other means.

Conductive Thread

Signals from an electrode are typically transmitted to an EEG device using standard metal wires, and such wires can be used with the present device 1. External wires, however, can become tangled, or can snag a protruding feature of something near the present device 1 and become disconnected, which can be a particular problem in less-controlled settings outside of a hospital. Therefore, in a preferred embodiment, an electrical connection between the electrodes 70 of the present device 1 and the wireless transmitter 300 is preferably accomplished with a conductive thread 75 integrated directly into the head strap 10.

Conductive thread is a thin, electrically conductive strand of material, typically having a diameter in the range of between about 0.5 millimeters (mm) and 5 mm, preferably from 2 mm to 4 mm in diameter. In some embodiments, the thread can comprise a non-conductive or less conductive substrate which is either coated or embedded with electrically conductive elements, often carbon, nickel, copper, gold, silver, or titanium. Substrates typically include cotton, polyester, or nylon. Preferably, conductive threads used with the present device 1 are sterilizable, such as with ethylene oxide.

The conductive threads 75 used in the present EEG headgear preferably comprise a non-ferromagnetic material, such as copper, silver, or tungsten. In this way, a patient wearing the EEG headgear can undergo testing with an MRI or CT scan device without needing to remove the present headgear. This is a particular advantage when the electrodes used with the present headgear are needle electrodes, since removal of the electrodes from the patient's skin in order to undergo an MRI or CT scan procedure would be both inconvenient and uncomfortable. The conductive thread is also preferably surrounded (wrapped) by an electrically insulating material, so that adjacent threads 75 or threads that cross each other on the head strap 10 do not electrically interfere with one another.

In one embodiment, a conductive thread comprising silver as the conductive material (i.e., silver conductive thread) can be used with the present device 1. The silver thread can comprise a nylon substrate coated or plated with silver, such as SHIELDEX thread (Statex Produktions+ and Vertriebs GmbH, Germany). Silver threads such as this are highly conductive, can be woven like thread, and have reasonably good tensile strength, having an elasticity up to 10 times greater than stainless steel wire of a similar diameter.

Figure 26:
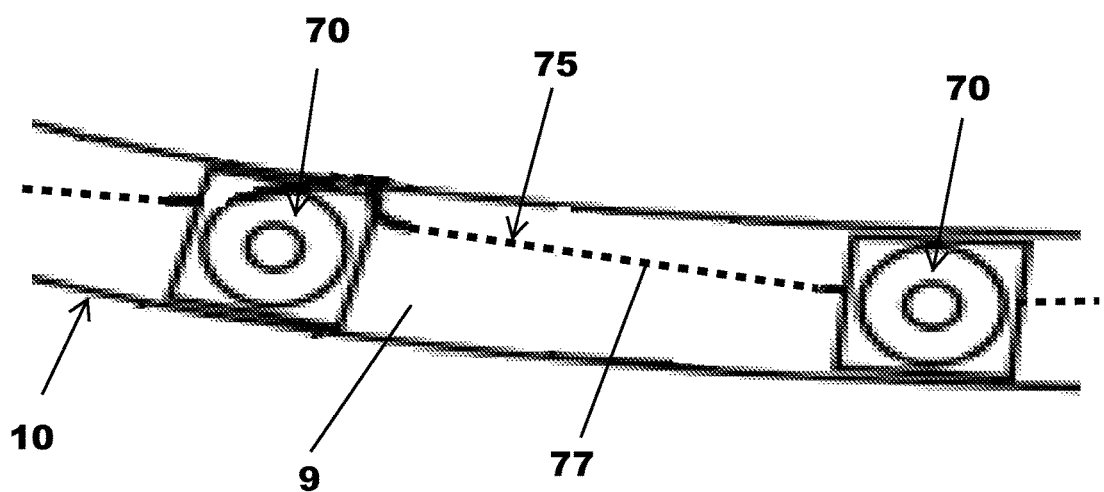
FIG. 26 is a top plan view of a head strap having electrodes electrically connected with conductive thread.

To attach conductive thread 75 to the head strap 10, the conductive thread is preferably sewn into the elastic substrate of the head strap 10, as shown in FIG. 26. An electrode end of the thread is placed into electrical communication with one of the electrodes 70, such as by soldering the thread 75 to the electrode, and an adjacent portion is placed through the head strap 10 in order to secure it to the head strap 10. A remainder of the conductive thread 75 can then be sewn into the cloth or other substrate of the head strap 10 until it reaches electrical connector 250 by looping the conductive thread from one surface of the head strap 10 to the other and back, i.e. from an outer surface 9 to an inner surface and back, thereby forming stitches 77 in the manner of sewing. Specifically, the conductive thread 75 can be passed from an outer (upper) surface 9 of the head strap 10 to an inner (lower) surface and then from the inner surface back to the outer surface 9 in a repetitive manner along a longitudinal extent, thereby forming stitches 77 and disposing the conductive thread in a sinuously curved manner along the extent of the head strap. A portion of the conductive thread between the point at which the thread exits a surface of the head strap and the point at which it next enters the head strap (in order to pass through to the other side of the strap) is a stitch 77, and the length of such stitches can be for example between 0.1 mm and 20 mm, preferably between 0.5 mm and 10 mm, more preferably between 1 mm and 5 mm, and even more preferably 2.5 mm to 3.5 mm.

In addition to maintaining the conductive thread in contact with or in close proximity to the surfaces of the head strap 10, thereby preventing the conductive thread from becoming snagged or tangled with other objects and/or from becoming disconnected from electrodes, the elasticity of the head strap is also maintained, because the conductive thread is disposed in sinuously curved, serpentine paths, i.e. in the typical waveform manner imbued by sewing when the thread is conducted from one side of the head strap to the other side and back again. With this sinuous arrangement, the slack formed by transversely disposed portions of the conductive thread allows the longitudinal spacing between peaks and valleys of the sinuously curved thread to increase (up until the point at which the conductive thread becomes essentially linear), i.e. by flattening the height of the thread's waveform, thereby allowing a portion of the head strap 10 to be lengthened without elastically deforming the conductive thread in a significant way, and thus allowing the elastic head strap 10 to be stretched to accommodate the head of a subject. Another way to put this is that the "wavelength" of the sinuously curved conductive thread increases when the head strap 10 is stretched and then decreases when the material in the head strap relaxes.

In an alternative embodiment, conductive threads can be sewn or otherwise disposed on another substrate, such as on a ribbon of material, which is itself then sewn or otherwise attached to the head strap 10. The conductive threads would in this case diverge (exit) from the ribbon of material when their respective designated connection point (an electrode or the wireless transmitter 300) is reached. Alternatively, a conductive thread that comprises a nonconductive substrate with sufficient elasticity to accommodate stretching of the head strap 10 can be used in the present device, either with or without being sewn onto the head strap 10.

Docking Station

As shown in FIGS. 10-14, the present EEG device 1 preferably includes a docking station 100 for retaining a wireless transmitter 300. The outer surface 137 of the docking station 100 is attached at a lower or bottom end 114 to the sagittal strap portion 20 and/or to the coronal strap portion 18 of the head strap 10. The docking station 100 is preferably attached to the head strap 10 at or near the point at which the head strap 10 contacts the crown of a subject's head, for reasons described further below.

The docking station 100 generally comprises a base or pedestal 110, a receptacle 130 for the wireless transmitter 300, and an electrical connector 250 for providing electrical communication between the wireless transmitter 300 and wires which connect to the electrodes 70 of the head strap 10. The receptacle 130 and its interior portion 135 can comprise any of a number of configurations capable of retaining the wireless transmitter 300 when it is placed in the interior portion 135 of the receptacle 130. In the embodiment shown in FIGS. 10-14, the receptacle comprises a generally rectangular interior space formed by a lower surface 134 of the receptacle 130 and the inner surface 133 of the side walls 136 of the receptacle 130, and is thus configured to retain a generally rectangular transmitter 300.

In this embodiment, the wireless transmitter can be retained by a friction fit with the inner surface 133 of the side walls 136 of the receptacle 130, but other retaining means such as clips, straps, ties, or other fasteners known to the art can also be used. A cover (not shown) placed over the wireless transmitter 300 and/or over the upper surface 132 of the receptacle 130 can also optionally be provided in order to protect and/or to help retain the wireless transmitter 300 within the receptacle 130. The cover could be secured to or integrally molded with the side walls 136, or could be reversibly secured to the receptacle 130, such as with hook and loop fasteners.

The docking station 100 further includes one or more openings 150 for receiving wired connections. In the embodiment shown in FIGS. 11-14, the electrical connector 250 and a plurality of wires 200 in electrical communication with the plurality of electrodes 70 of the present device 1 are placed in communication with the interior 135 of the receptacle 135 through an opening 152 in the rear face of the docking station 100. When the present device is in use, the wireless transmitter 300 is connected to the electrodes 70 by means of a reversible connection with the electrical connector 250. The electrical connector can be, for example, a jack such as a 10 pin connector having a distal receiving end 251 in communication with the interior of the receptacle 130. The transmitter 300 is provided with a mating electrical connector, for example a plug (210, shown in FIG. 17).

Each of the wires 200 (which can be conductive threads) connected to respective electrodes 70 connect at the proximal end 253 of the electrical connector 250. Preferably, the wires or conductive threads are protected by a covering, such as a wrapped or molded plastic layer when they extend away from the head strap 10 to the electrical connector 250.

A second opening 151 is also preferably provided at the front end of the docking station 100 to allow wired access to a second connector (212, FIG. 18) on the wireless transmitter 300 while it is retained within the receptacle 130. The second connector 212 is preferably an 8 pin port to allow charging of the transmitter 300 while it is retained in the docking station 100. Alternatively or in addition, the second connector can be used to communicate with the transmitter 300 and program the transmitter's firmware, for example.

For hygienic purposes, the portions of the present system with which a subject might come into contact, namely the docking station 100 and head strap 10, are preferably made from relatively low-cost materials that can be disposed of after use. The docking station 100, for example, can be formed from an expanded, rubberized polymer foam material such as ethylene-vinyl acetate (EVA), expanded polyethylene foam, or expanded polypropylene foam. The use of a foam material also provides the advantages of being light as well as being soft and therefore more comfortable when worn by a patient. Foam materials also provide shock resistance and thus better protect the transmitter 300.

In addition, the material used to form at least the base 110 of the device, and preferably also the receptacle 130, is preferably transparent to X-rays such that the material absorbs, scatters and/or reflects less than 20% of the X-ray radiation it receives, more preferably less than 10% of such radiation, and even more preferably less than 1%. When the base 110 of the docking station 100 is placed at the crown of a subject's head and is formed from a material which is substantially transparent to X-rays, a subject wearing the head strap 10 and docking station 100 of the present EEG device 1 can be placed within a CT scanner and receive a CT scan without needing to remove the present EEG device. This is advantageous because an EEG may provide an indication that further imaging (such as a CT scan) is needed, and in this case a subject can receive the scan without having to remove the EEG device from the patient, so that the patient's brain activity can continue to be monitored with the present device following the CT scan. Alternatively, an X-ray image can be obtained while a subject is wearing the head strap 10 and docking station 100 of the present device 1.

In a particularly preferred embodiment, the base 110 is a pedestal having a thickness greater than the walls of the receptacle 130 of the docking station 100. By providing such a pedestal for the docking station 100, the wireless transmitter 300 is retained further from the top of a subject's head, thereby reducing the possibility of interference between the wireless transmitter 300 and a CT scanner during a CT scan of the subject. The pedestal can for example be between 6 millimeters and 3 centimeters in thickness, but is preferably between 1.3 centimeters and 2.5 centimeters thick. In some embodiments, the base 110 and receptacle 130 can be integrally formed, such as by molding.

Wireless Transmitter

Figure 15:
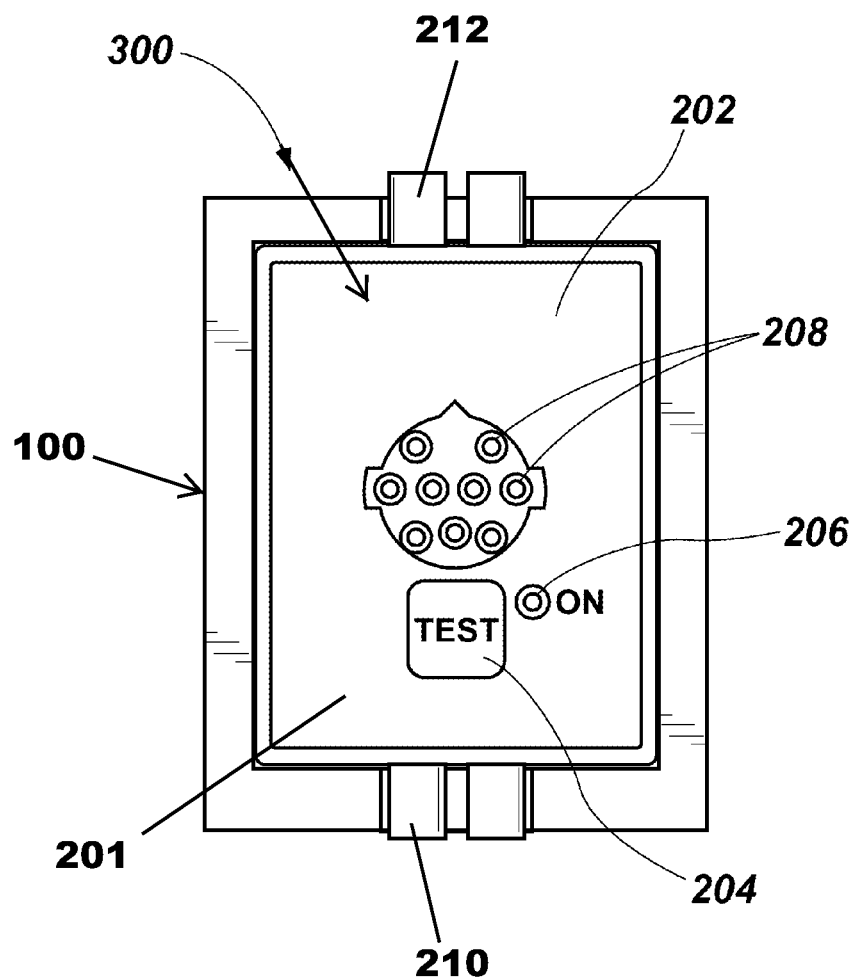
FIG. 15 is a top plan view of the transmitter of the present EEG device.
Figure 16:
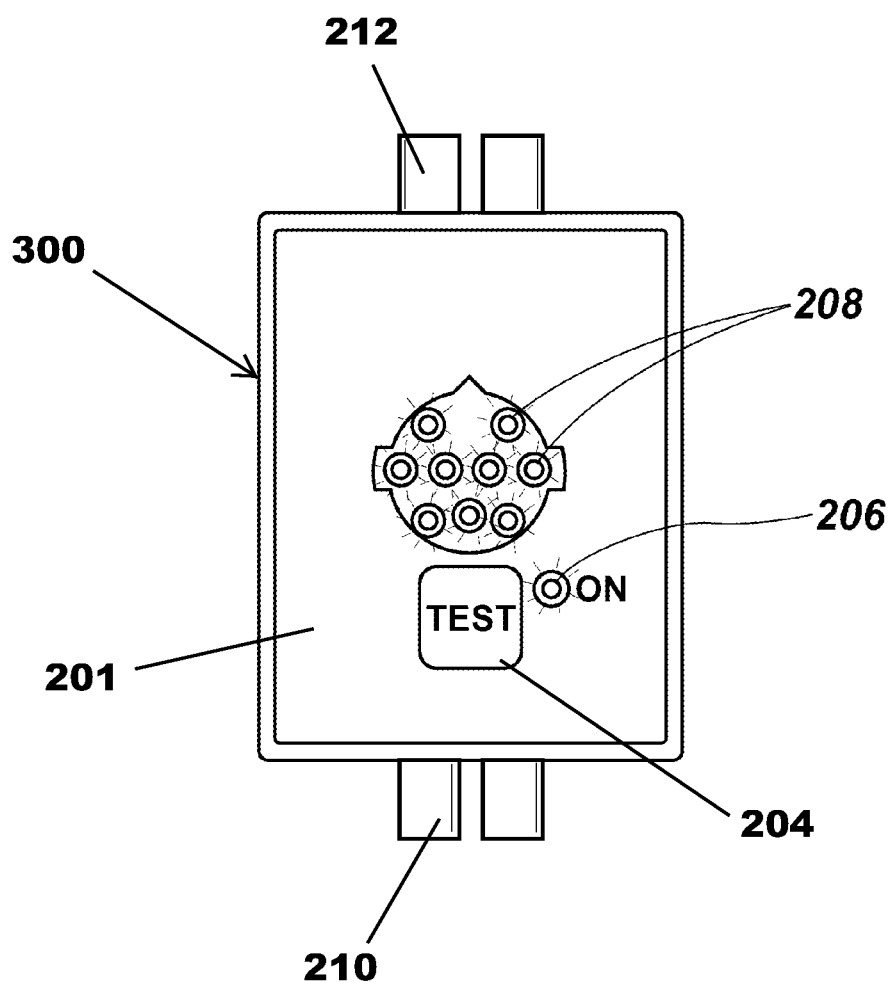

The wireless transmitter 300 that is retained by the docking station 100 is adapted to facilitate both wireless and wired transmissions to a processing system. As shown in FIG. 15, the transmitter 300 has a top surface 201 with a user interface 202. In the depicted embodiment, the user interface 202 includes a test input 204, a power indicator 206 and one or more electrode impedance indicators 208. The power indicator 206 is adapted to indicate whether the transmitter is powered ON or OFF. In the depicted example, the power indicator 206 is implemented as a light, as shown in FIG. 16. In this example, the light turns on when the transmitter 300 is powered ON.

As shown in FIGS. 15 and 16, the electrode impedance indicators 208 are adapted to indicate to a user whether the impedance of a particular electrode 70 is above some threshold level. Each indicator 208 is associated with a specific electrode 70 so the user can identify which, if any, electrodes 70 are experiencing poor impedance. In the depicted example, the electrode impedance indicators 208 are LED lights located relative to one another so as to correlates to the relative position of the respective electrode 70 on the subject's head, and are disposed within a graphic image depicting a top plan view of a subject's head. These lights can glow one color (e.g., green) when impedance levels for a respective electrode 70 is below a predefined threshold, and can glow a different color (e.g., red) when the impedance level is above the predefined threshold. In some embodiments, the predefined threshold is about 15 kilohms, so that an impedance level below 15 kilohms will cause the indicator 208 to indicate the impedance is acceptable, while an impedance above 15 kilohms will cause the indicator 208 to indicate the impedance is not acceptable.

Figure 17:
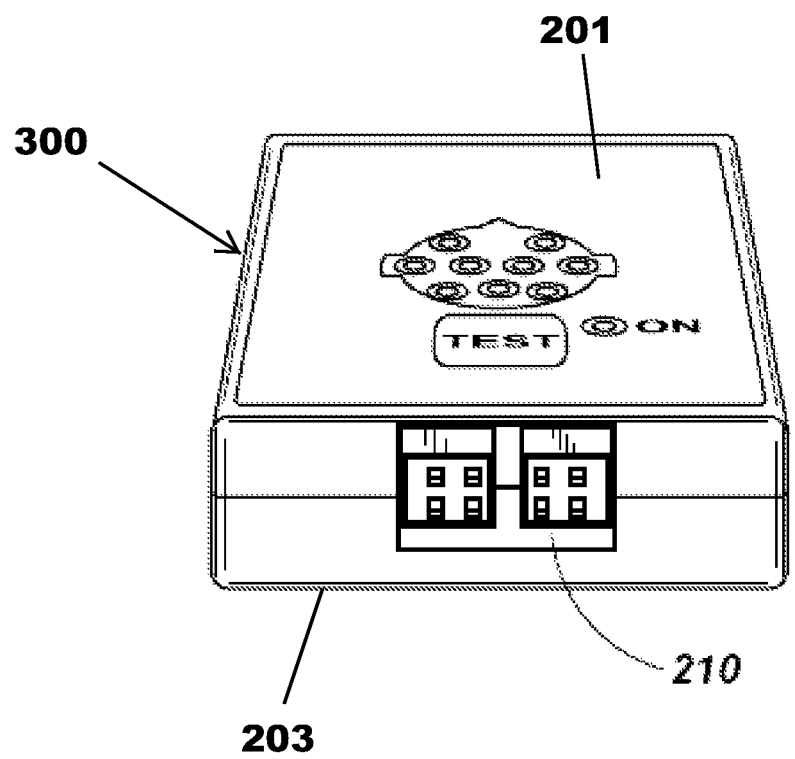
FIG. 17 is a rear perspective view of the transmitter of FIG. 15.

The transmitter 300 includes an electrode interface 210 shown in FIG. 17 for facilitating electrical communication with each of the electrodes 70. In this manner signals can be conveyed between (e.g., from) each electrode 70 and the transmitter 300.

Figure 18:
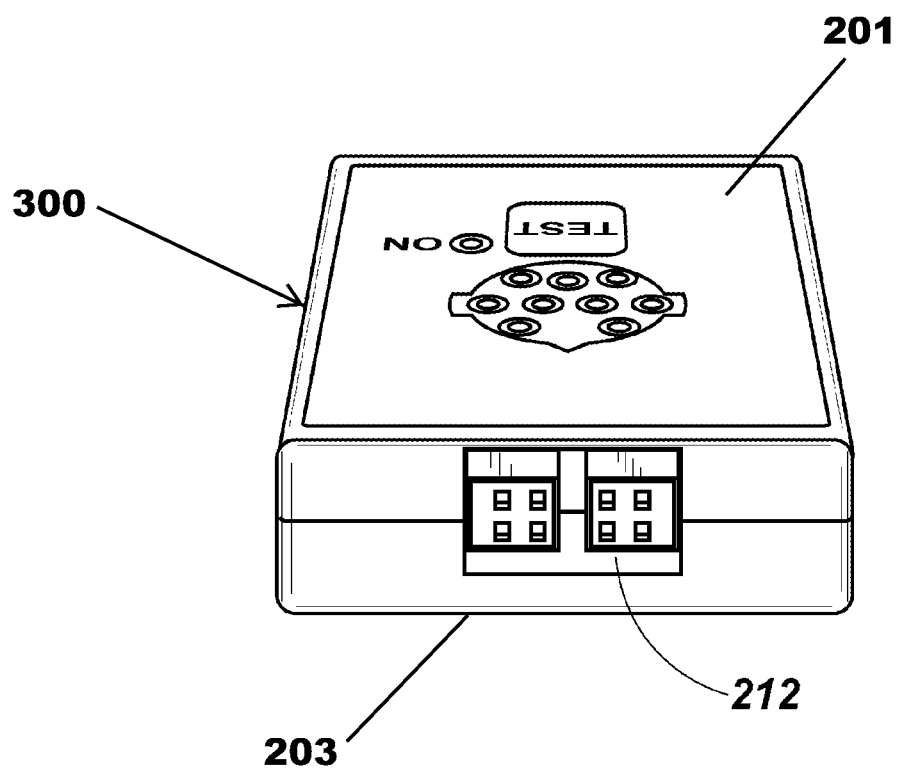
FIG. 18 is a front perspective view of the transmitter of FIG. 15.

The transmitter 300 can also include a remote device interface 212 shown in FIG. 18 and adapted to couple the transmitter 300 with a remote device through a wired connection. In this manner, the transmitter 300 can be communicatively coupled via a wired connection with one or more remote devices.

Figure 19:
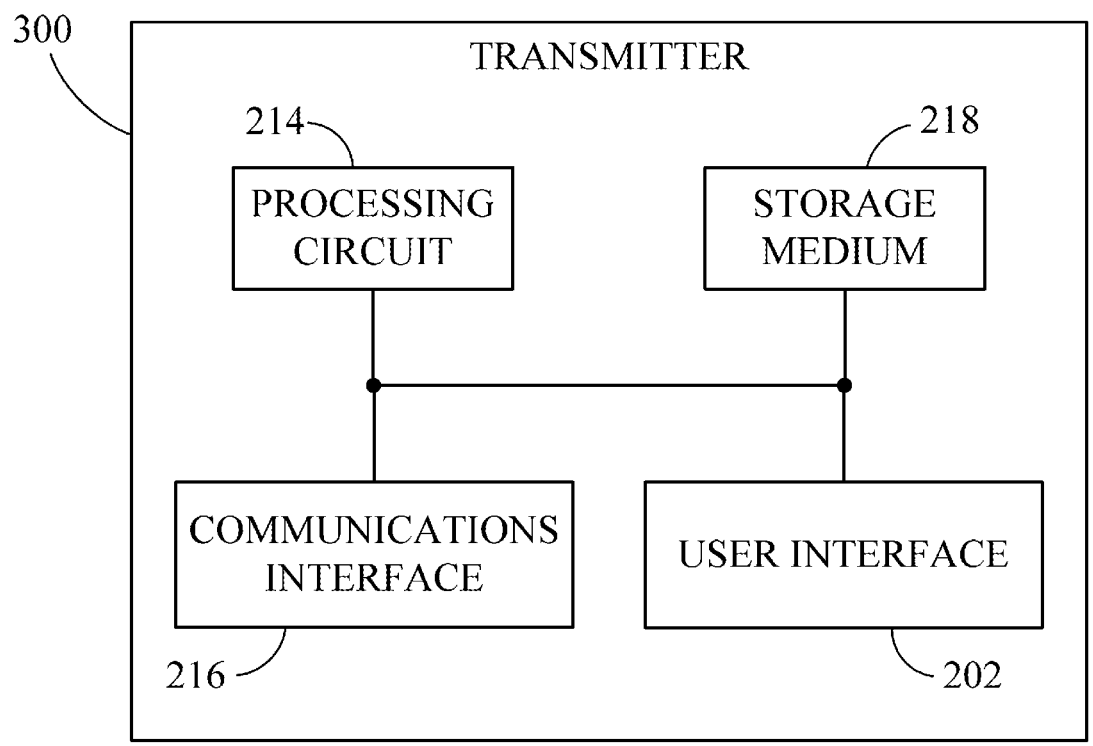
FIG. 19 is a block diagram of the transmitter of FIG. 15 in communication with a receiver.

FIG. 19 shows a block diagram of the transmitter 300 according to at least one embodiment. The transmitter 300 includes a processing circuit 214 coupled to or placed in electrical communication with a communications interface 216, a storage medium 218, and a user interface 220.

The processing circuit 214 is adapted for processing, including the execution of programming, which may be stored on the storage medium 218. Accordingly, the processing circuit 214 is arranged to obtain, process and/or send data, control data access and storage, issue commands, and control other desired operations. The processing circuit 214 may include circuitry configured to implement desired programming provided by appropriate media in at least one example. For example, the processing circuit 214 may be implemented as one or more processors, one or more controllers, and/or other structure configured to execute executable programming. Examples of the processing circuit 214 may include a general purpose processor, a digital signal processor (DSP), an application specific integrated circuit (ASIC), a field programmable gate array (FPGA) or other programmable logic component, discrete gate or transistor logic, discrete hardware components, or any combination thereof designed to perform the functions described herein. A general purpose processor may include a microprocessor, as well as any conventional processor, controller, microcontroller, or state machine. The processing circuit 214 may also be implemented as a combination of computing components, such as a combination of a DSP and a microprocessor, a number of microprocessors, one or more microprocessors in conjunction with a DSP core, an ASIC and a microprocessor, or any other number of varying configurations. These examples of the processing circuit 214 are for illustration and other suitable configurations within the scope of the present disclosure are also contemplated.

According to one or more aspects of the present disclosure, the processing circuit 214 may be adapted to perform (in conjunction with the storage medium 218) any or all of the processes, functions, steps and/or routines described herein for the transmitter 300.

The communications interface 216 is configured to implement wireless and/or wired communications of the transmitter 300. For example, in some embodiments, the communications interface 216 can be configured to communicate information bi-directionally with respect to one or more other devices (e.g., another processing system). The communications interface 216 can be coupled with an antenna (not shown) and can include wireless transceiver circuitry for wireless communications with wireless devices. In some embodiments, the wireless transceiver circuitry is configured to facilitate Bluetooth communications. In other embodiments, the wireless transceiver circuitry can be configured to facilitate other wireless communications, such as WiFi, Zigbee, Wireless USB, or other wireless wide area network (WWAN) standards, wireless local area network (WLAN) standards, and/or wireless personal area network (WPAN) standards. The communications interface 216 can also include a network interface (e.g., a network interface card (NIC)) for the electrode interface 210 shown in FIG. 17 and the remote device interface 212 shown in FIG. 18. The network interface may be implemented as a serial or parallel connection, a USB port, a Firewire interface, a flash memory interface, a floppy disk drive, or any other suitable arrangement for communicating with respect to public (e.g., Internet) and/or private networks or other wired arrangements.

The storage medium 218 may represent one or more computer-readable, machine-readable, and/or processor-readable devices for storing programming, such as processor executable code or instructions (e.g., software, firmware), electronic data, databases, or other digital information. The storage medium 218 may also be used for storing data that is manipulated by the processing circuit 214 when executing programming. The storage medium 218 may be any available media that can be accessed by a general purpose or special purpose processor, including portable or fixed storage devices, optical storage devices, and various other mediums capable of storing, containing or carrying programming. By way of example and not limitation, the storage medium 218 may include a computer-readable, machine-readable, and/or processor-readable storage medium such as a magnetic storage device (e.g., hard disk, floppy disk, magnetic strip), an optical storage medium (e.g., compact disk (CD), digital versatile disk (DVD)), a smart card, a flash memory device (e.g., card, stick, key drive), random access memory (RAM), read only memory (ROM), programmable ROM (PROM), erasable PROM (EPROM), electrically erasable PROM (EEPROM), a register, a removable disk, and/or other mediums for storing programming, as well as any combination thereof.

The storage medium 218 may be coupled to the processing circuit 214 such that the processing circuit 214 can read information from, and write information to, the storage medium 218. That is, the storage medium 218 can be coupled to the processing circuit 214 so that the storage medium 218 is at least accessible by the processing circuit 214, including examples where the storage medium 218 is integral to the processing circuit 214 and/or examples where the storage medium 218 is separate from the processing circuit 214 (e.g., resident in the transmitter 300, external to the transmitter 300, distributed across multiple entities).

As noted above, the user interface 202 includes the test input 204, the power indicator 206 and one or more electrode impedance indicators 208 shown in FIG. 15. Although the embodiment in FIG. 15 employs LEDs for the power indicator 206 and the electrode impedance indicators 208, other indicators may be employed. For example, the electrode impedance indicators 208 may include any display capable of visually indicating to a user that an impedance value is above some predetermined threshold, such as a spectrum display showing relative impedance values, an LED or LCD screen, etc.

In some embodiments, the user interface 202 may include an audio impedance indicator adapted to provide an audio indication (e.g., a buzzing sound, a beeping sound, etc.) when an impedance value for one or more electrodes is above the predetermined threshold. For example, the user interface 202 may include an audio transducer coupled with the processing circuit 214. The processing circuit 214 can cause the audio transducer to generate an audible noise when an impedance value of one or more electrodes is above the predetermined threshold. The audible noise can aid in drawing a user's attention to the occurrence of unacceptably high impedance in one or more electrodes, and the electrode impedance indicators 208 can identify to the user which electrode(s) are exhibiting the high impedance.

Figure 20:
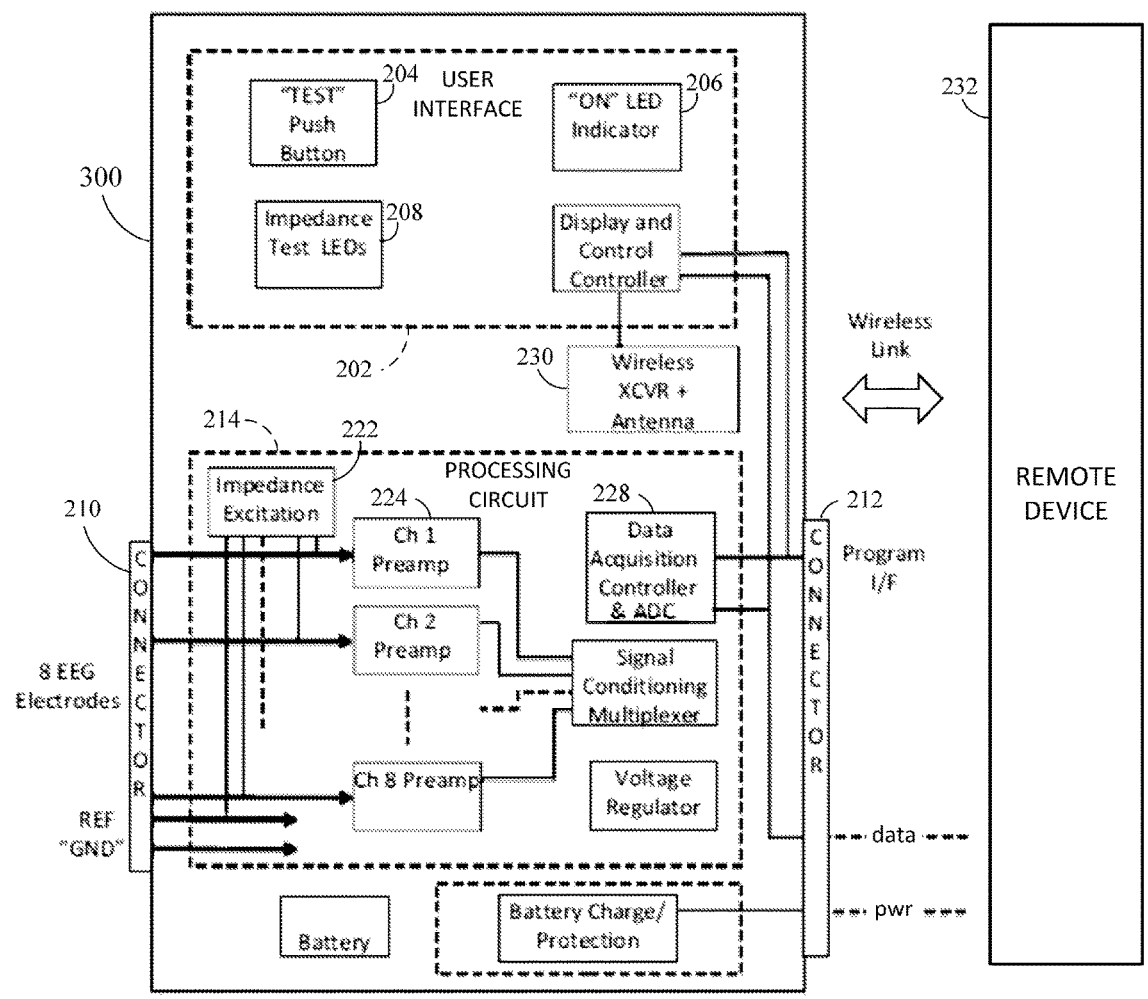
FIG. 20 is a block diagram of at least some components of the transmitter of FIG. 19 in one embodiment.

Turning to FIG. 20, a more detailed block diagram is shown according to at least one embodiment of the transmitter 300. As shown, the processing circuit 214 may include an impedance excitation module 222, a plurality of preamps 224, a signal conditioning multiplexer 226, and a data acquisition controller and analog-to-digital converter (ADC) 228. In at least one embodiment, the processing circuit 214 can be implemented with an integrated circuit chip, such as one of the integrated circuits sold under the names ADS 1294R, ADS 1296R, or ADS 1298R by TEXAS INSTRUMENTS. These integrated circuits include multi-channel, simultaneous sampling, 24-bit delta-sigma analog-to-digital converters (ADCs) with built-in programmable gain amplifiers (PGAs), internal reference, and an onboard oscillator commonly employed in medical electrocardiogram (ECG) and electroencephalogram (EEG) applications. In other embodiments, one or more of the forgoing modules and elements may be implemented as separate and individual circuits and/or modules.

In operation, the transmitter 300 receives respective electrical signals from a plurality of electrodes 70 (e.g., eight in FIG. 20) via the electrode interface 210 of the communications interface 216. These received signals represent the electrical signals each electrode 70 received from the subject's brain, and may be referred to as brain signals. These signals are amplified at a preamp 224, and the amplified signals can be converted from analog to digital signals in the analog-to-digital converter 228.

The digital signals for each electrode signal can be transmitted to a remote device 232 through the wireless transceiver 230. In some embodiments, the digital signals are transmitted by means of a Bluetooth transmission. In other embodiments, the digital signals are transmitted by means of a wired connection, such as a cable coupled to the remote device interface 212 and also coupled to the remote device 232.

The transmitter 300 also measures an impedance for each electrode 70. The impedance measurements can be used to determine whether the electrodes 70 are properly coupled to the subject's head and/or are functioning properly. A high impedance may indicate that the electrode 70 is not sufficiently coupled to the subject's head, that the electrode 70 is not functioning well or properly, or that the electrode 70 is defective for some reason. For instance, a needle, disc or cup electrode that has come loose from the subject's scalp will exhibit relatively high impedance. Similarly, if the conductive liquid, hydrogel or solid gel of a wet electrode has dried out, the electrode will typically exhibit relatively high impedance. Furthermore, an electrode that is coupled to a broken or otherwise defective conductive thread may exhibit relatively high impedance.

To obtain the impedance measurements, the impedance excitation module 222 can inject a DC or AC current into each of the electrodes 70. The processing circuit 214 can then measure the voltage generated for each electrode 70 from the injected current to determine an impedance value with respect to the reference signal. The processing circuit 214 can then determine whether each respective impedance value is above or below a predefined threshold. In at least some embodiments, the impedance measurements can be obtained at least substantially simultaneously with receiving the electrical signals each electrode 70 receives from the subject's brain.

According to at least one aspect, the transmitter 300 can visually display via an electrode impedance indicator 208 whether the impedance associated with each electrode is above or below a predetermined threshold. For instance, the processing circuit 214 can cause a respective impedance test LED in the user interface 202 to indicate that the impedance for the particular electrode 70 is within an allowable range (e.g., below 15 kilohms) or outside of an allowable range (e.g., above 15 kilohms).

According to at least one aspect, the transmitter 300 can wirelessly transmit the measured impedance values associated with each electrode 70 via the wireless transceiver 230. These measured impedance values can be sent at least substantially simultaneously with the signals from each electrode 70 obtained from the subject's brain. For Bluetooth transmissions, the wireless signals are transmitted in a 2.4 gigahertz frequency (e.g., 2.4-2.48 gigahertz). When the wireless transceiver 230 transmits the brain signals from each electrode 70 using Bluetooth transmissions (e.g., over various channels in the range of 2.4 gigahertz to 2.48 gigahertz), the measured impedance values for each electrode 70 can be transmitted at least substantially simultaneously as a 62.5 hertz waveform on top of the Bluetooth signal. In at least some instances, the amplitude of the 62.5 hertz waveform can be roughly inversely proportional to the impedance value. In some embodiments, the wireless transmission of the measured impedance values can be turned on or off at the transmitter by a user.

The remote device 232 can receive the transmission including the two data streams and can filter out the measured impedance values from the brain signals for processing each of the signals independently.

As a result of the transmitter 300 measuring the impedance at least substantially continuously, the transmitter 300 and/or the remote device 232 can employ the impedance measurements for conditioning the signals before the signals are processed. For example, the transmitter 300 and/or the remote device 232 can employ the impedance values associated with a respective electrode to boost (e.g., amplify) the electrical signals received from the respective electrode.

Figure 21:
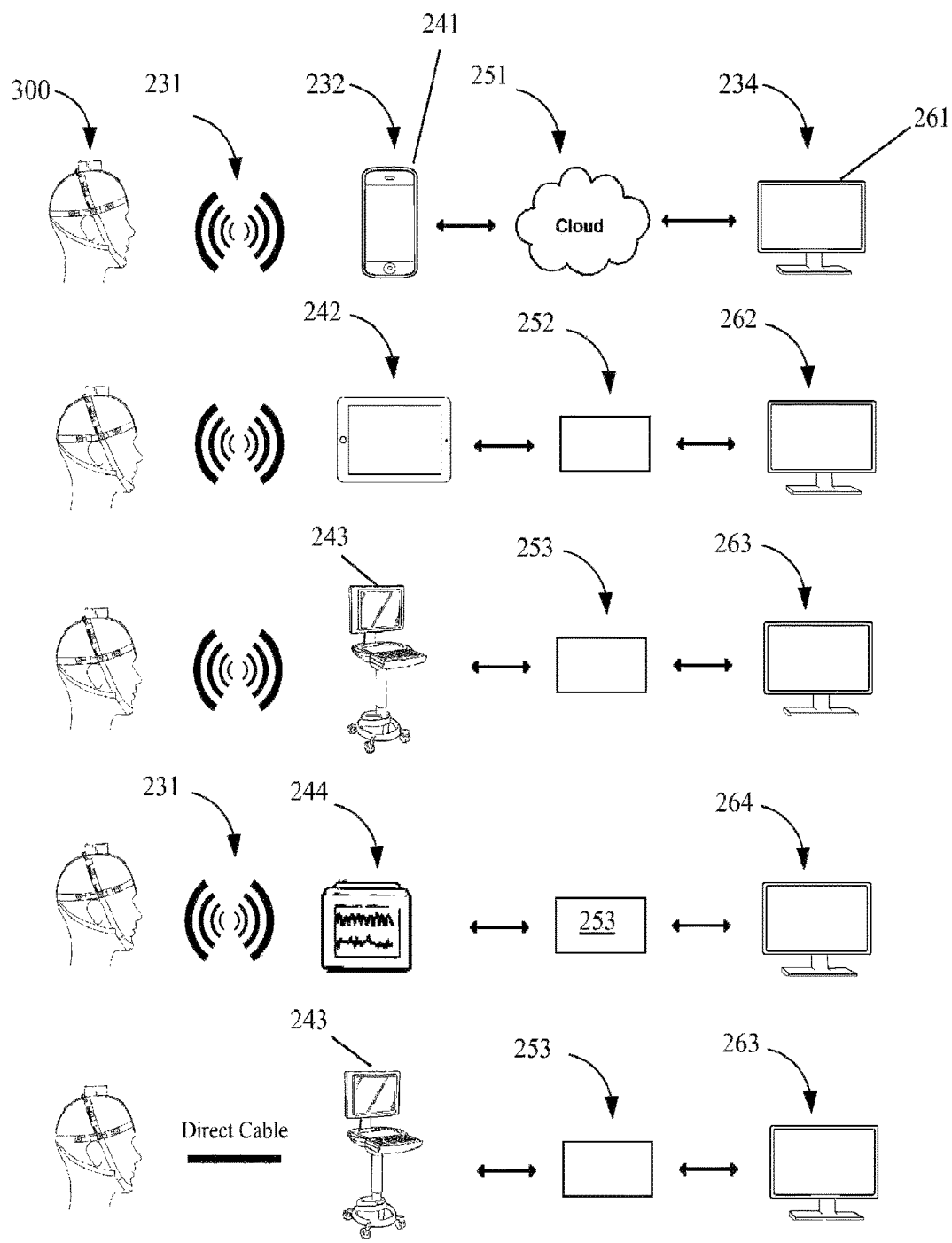
FIG. 21 is a block diagram of some examples of network environments in which the transmitter of FIG. 15 can operate.

As shown in FIG. 21, the transmitter 300 can be employed in a variety of different network environments. Generally speaking, the transmitter 300 can convey the electrical brain signals and respective impedance values from each electrode to a remote device. In various examples, the transmitter 300 can convey such information wirelessly via a wireless wide area network (WWAN), a wireless local area network (WLAN), and/or a wireless personal area network (WPAN). In at least some embodiments, the transmitter 300 communicates with the remote device 232 via a WPAN employing Bluetooth communication standards. In other embodiments, the transmitter 300 communicates with the remote device 232 via a wired network, such as a direct cable coupled between the transmitter 300 and the remote device 232.

As illustrated in FIG. 21, the transmitter 300 can, for example, transmit signals via a Bluetooth signal 231 or other short-range communication standard to a remote device 232 such as a smartphone 241, a tablet computer 242, a laptop computer, an existing EEG acquisition device 243, or a vital-sign monitor 244. The remote device 232 can be configured to process the received signals and generate one or more visual outputs for a user to evaluate. Alternatively, the transmitter 300 can be connected by a wired (cable) connection to another device.

In some instances, the remote device 232 can further convey the received information and/or additional information determined from the received information to one or more other devices and/or displays 234. The remote device 232 may convey the received and/or additional information via a wide area network (WAN), a local area network (LAN), a personal area network (PAN), including one or more combinations thereof. Such networks may include wireless and/or wired networks. FIG. 21 shows some non-limiting examples including via a cloud network 251, a dedicated network 252, a hospital network 253 and/or a monitoring system network 254.

The one or more other devices and/or displays 234 can include additional processing systems similar to the remote devices 232, as well as displays. Some non-limiting examples include a computer 261 (e.g., laptop, desktop, tablet, etc.), a nurses station ICU monitoring system 262, an EEG review station 263, and a generic display 264. Although specific combinations are depicted in FIG. 21, it will be apparent that other combinations of the depicted examples, as well as combinations including different networks and/or devices are also possible.

Although the various examples refer to transmissions sent by the transmitter 300, the transmitter 300 can also be adapted to receive communications via a wireless or wired network. For example, the transmitter 300 may receive communications from a remote device 232 via a WPAN employing Bluetooth communication standards and/or via a wired network. Such communications can, for example, enable the transmitter 300 to be remotely controlled. For instance, a remote device 232 may enable or disable the impedance measurement operations of the transmitter 300 and/or modify one or more operating parameters including gain, initiation of a memory dump, or powering down.

Simplified EEG Interface

In order to detect medical conditions with an EEG, waveforms which have relatively uniform morphology and duration are detected, and the interval between consecutive waveforms is determined. In particular, waveforms which occur at regular intervals can be indicative of a condition in need of treatment. Waveforms being detected are preferably consistent and of greater amplitude than other waves, with the amplitude being relatively consistent. A range of the ratio of the amplitude of the wave to the amplitude of the interval (Amp W/Amp I) can be used to define particular waveforms of interest, with a relative standard deviation measure of this ratio being used to determine the consistency of the waveform.

EEG's are typically displayed as a graph comprising a series of lines showing waves of varying amplitude and wavelength in linear form, with each line corresponding to a signal received from an electrode of an EEG device. In order to interpret whether such waveform patterns present an indication of a brain injury or other medical condition, they must be evaluated by a trained technician or expert.

The present system preferably comprises a simplified user interface 400 for evaluating EEG readings. This interface provides rapid, accurate and more easily interpreted information to a medic or other user of the present system regarding the nature and severity of any EEG abnormalities measured by the present system, thereby reducing the need to analyze more complex waveform patterns displayed in typical EEG readings and increasing medical response times. In addition, the present interface 400 can display brain wave pattern information in a dynamic format, providing continuous EEG monitoring data during transport of a subject and during therapeutic interventions.

In order to create such a simplified interface, EEG data from electrodes measuring data from each hemisphere of a subject's brain is first analyzed separately, such as by a microprocessor, in predetermined time segments, in order to determine whether predetermined waveform patterns are present in each time segment. Such predetermined segments preferably range between 5 seconds and 20 seconds, and are advantageously 10 seconds in length. Waveform patterns are preferably analyzed to determine whether they correspond to patterns associated with clinically significant, moderate to severe, acute or progressive brain damage. These patterns, which are known to those skilled in the art, include suppression, slowing, burst-suppression, inter-hemisphere asymmetry, periodic epileptiform discharges (PEDS), and seizure. Algorithms for determining these waveform patterns are likewise known [see, e.g., Claasen, J, et al., "Quantitative Continuous EEG for detecting delayed cerebral ischemia in patients with poor grade subarachnoid hemorrhage," Clinical Neurophysiology, 2004, 115:2699-2710; Steward C P, et al., Seizure identification in the ICU using quantitative EEG displays," Neurology, 2010, 75:1501-1506; Zandi A S, et al., "Automated real-time epileptic seizure detection in scalp EEG recordings using an algorithm based on wavelet packet transform," IEEE Trans Biomed Eng., 2010, 57(7):1639-1651; White, A M, et al., "Efficient unsupervised algorithms for the detection of seizures in continuous EEG recordings from rats after brain injury," Journal of Neuroscience Methods, 2006, 152:255-266].

Figure 24:
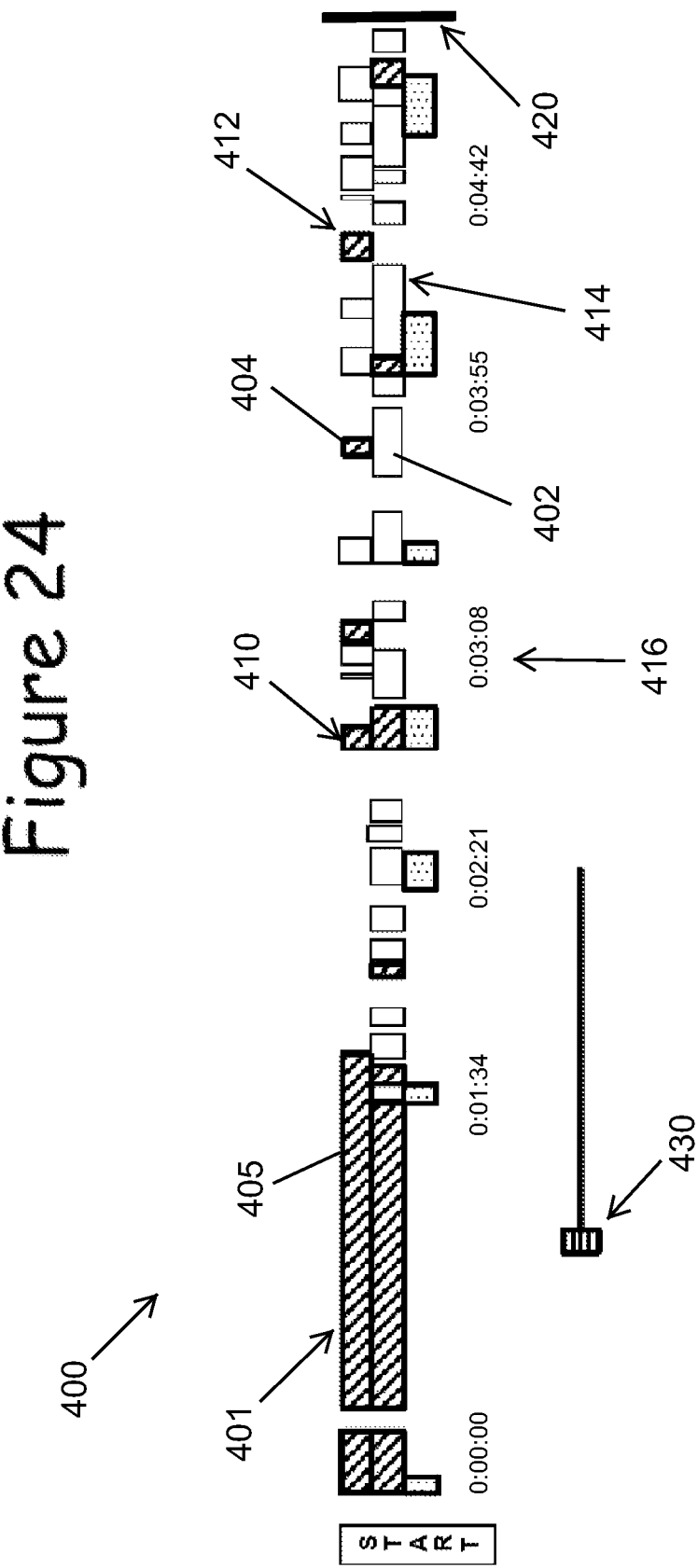
FIG. 24 is an illustration of another user interface for reviewing EEG data.

When data from a particular time segment is found to match the pattern for one of the predetermined waveform patterns, it is displayed using an indicator from a predetermined set of visually distinguishable indicia, for example visually distinguishable colors, patterns, shadings, and/or other visual referents. In one embodiment, the simplified interface displays a predetermined color to indicate a waveform pattern. For example, a waveform pattern indicative of a seizure might be displayed with the color red (as indicated with white bars 402 in FIG. 24), while waveform patterns in a normal range might be displayed in blue (indicated in FIG. 24 with bars 404 having parallel lines). The graphical form of the indicia associated with such displayed color can take any of a number of forms. In the form shown in FIGS. 24 and 25, the colored indicia are displayed as vertical bars 410 which are set out horizontally in temporal order to form indicia sets 401. As can be seen in FIG. 24, the indicator is displayed as a single bar when a single time segment corresponds to the predetermined wave pattern, as shown by the blue bar 405 in FIG. 24. When multiple time segments correspond to the same wave pattern, they can be indicated as a series of separate indicia, but in a preferred embodiment are indicated as a continuous band of colored indicia having a length equal to the sum of the number of indicia that correspond to the wave pattern, as with the plurality of indicia indicated by the horizontal band 405 in FIG. 24, made up of a plurality of vertical bars 410. Separate indicia sets 401 are displayed for the right and left hemispheres of a subject's brain, shown as left hemisphere indicia set 412 and right hemisphere indicia set 414 in FIG. 24.

The present interface 400 preferably shows a moving display of brain wave patterns over time as in the display of FIG. 24. A vertical time bar 420 preferably tracks the time point (in real time or recorded time) at which a brain wave pattern has been detected. The time bar preferably tracks both hemispheres of a subject's brain together in parallel, i.e. with the time bar 420 intersecting the indicia for a predetermined point of time for the subject's right hemisphere and also intersecting the indicia for the same point of time for the subject's left hemisphere. An indicator of actual or elapsed testing time 416 can be included in parallel with the indicia sets 400. In order to review the progress of an EEG, the portion of the analyzed EEG indicia sets 401 viewable in the interface window can be manipulated, such as with scrolling bar 430. Scrolling through the indicia sets in this way can assist a technician or other expert viewing the EEG to identify trends quickly.

Figure 22:
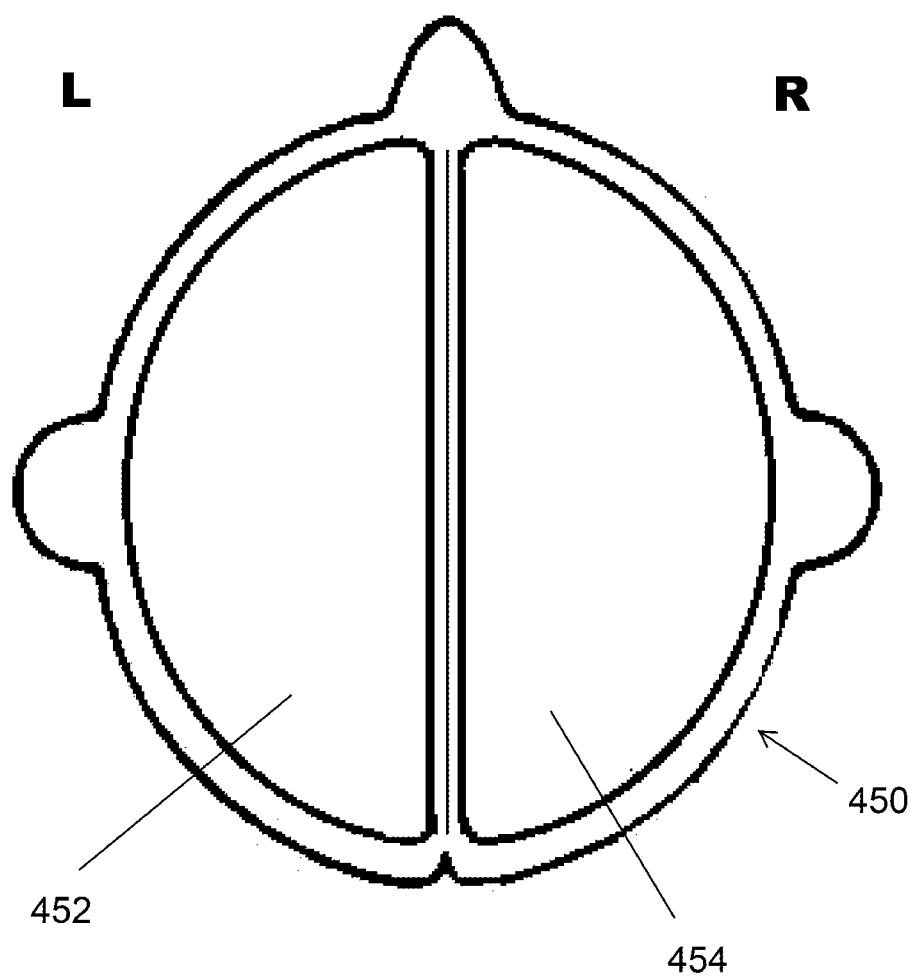
FIG. 22 is an illustration of a simplified user interface for reviewing EEG data.

As shown in FIG. 22, the present interface further preferably comprises a simplified user interface comprising a graphic 450 having two distinct, predetermined portions or display areas, preferably a right half 454 and left half 452. In FIG. 22 the graphic 450 is in the form of a top plan view of a head and the right and left hemispheres of a brain in stylized form. The display areas 455 display the color of the indicia corresponding to a particular time segment of the EEG, such as the segment represented by the "blue" bar 410 in FIG. 24. As shown in FIG. 24, during the time segment corresponding to the bar 410, the subject's left hemisphere is experiencing a wave pattern indicated by the color blue, while the subject's right hemisphere is experiencing a pattern indicated with the color red (bar 402). When the graphic 450 is used with the indicia sets 401, when the time bar 420 is at the time segment of bar 410, the graphic 450 is likewise colored to indicate that the subject's left hemisphere is experiencing a brain wave pattern indicated by the color blue while the subject's right hemisphere is experiencing a pattern indicated by the color red. It has been found that displaying wave pattern information with both the temporally displayed indicia sets 401 and the graphical representation 450 facilitates a more rapid and accurate determination of the status of a subject's brain.

Figure 23:
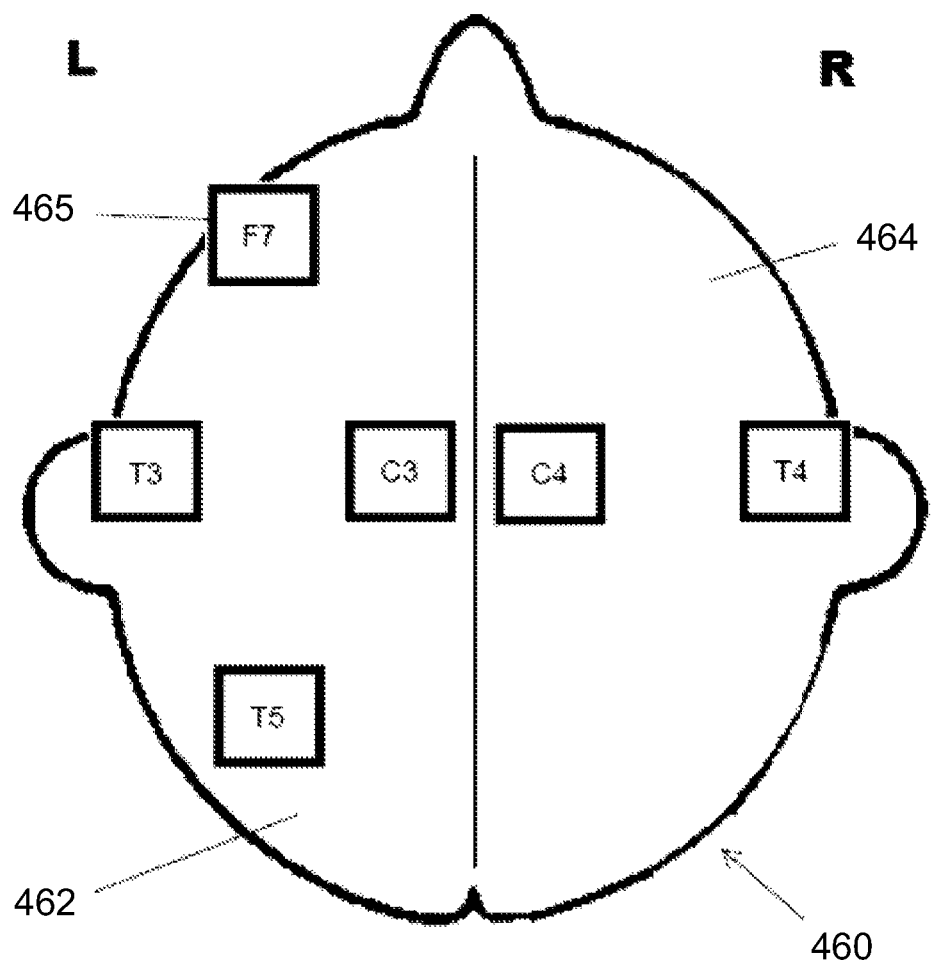
FIG. 23 is an illustration of a user interface showing impedance data of the electrodes of an EEG device.

In a preferred embodiment, as shown in FIG. 23, the interface 400 can also include an electrode status display with a continuous or periodically updated indicator of the integrity of each electrode. Like the graphic 450, the electrode status display 460 preferably has two distinct portions or display areas, such as a right half 464 and left half 462, which are also likewise in the form of the outline of the top of a human head. The appearance of a graphic or other indicia 465 corresponding to a particular electrode of the associated EEG device can indicate a rising impedance or disconnection of that electrode, and thereby inform a technician obtaining the EEG that the electrode needs to be reattached or replaced.

Figure 25:
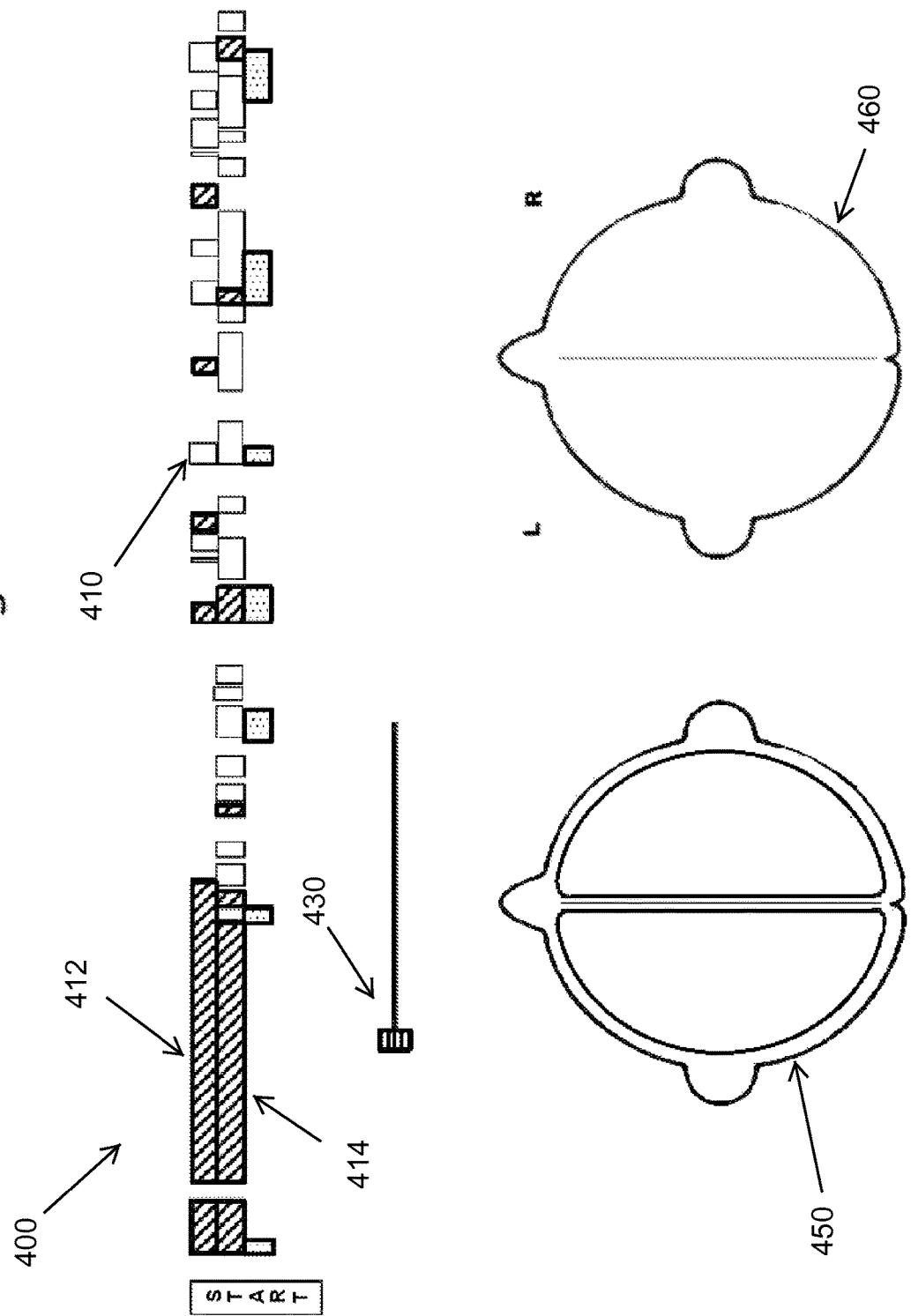
FIG. 25 is an illustration of a preferred user interface for reviewing EEG data.

A preferred embodiment of the present interface is shown in FIG. 25. In this embodiment the interface includes a real-time, continuously running, and color-coded landscape view of the EEG analysis in the form of the indicia sets 401 at the top of the screen. Below the landscape view are two schematized head views 450 and 460 (as seen from the vertex divided into left and right hemispheres), with the hemispheres of the graphic 450 filled in with colors corresponding to the specific abnormal patterns detected over time and the graphic 460 displaying no indicia (indicating that all electrodes of the EEG device are functioning). The right head view 460 displays the presence of excessive 60 Hz or baseline sway artifacts from recording electrodes.

Methods of Use

The present device has applications in any of a number of emergency situations, but particularly those that are currently underserved due to the difficulty of setting up EEG electrodes on a subject's scalp and the lack of availability of equipment adapted for emergency environments. One such environment is the battlefield, where head trauma and resulting brain injury are all too common. Traumatic brain injury may not be easily detected early on, as mental status testing can be subjective and depend on the examiner and the subject. Symptoms of brain injury can also resemble psychological reactions, so signs of such injury may not be immediately detectable in the absence of EEG. If undetected and left untreated, such injuries may progress to secondary brain injuries such as traumatic cerebral contusions (TCC), intra-parenchymal hemorrhages (IPH), epidural hematomas, acute subdural hematomas (SDH), secondary ischemic stroke, or seizures. In non-military situations, the present EEG device has particular use in view of its ease of set-up and use for evaluating hypothermia for post-cardiac arrest comatose survivors; managing acute traumatic brain injury in hospital emergency departments; diagnosing coma and seizures in emergency departments; treating status epilepticus in the field; diagnosing acute sport concussions; monitoring hospital stroke and stroke-at-risk patients; and neonatal ICU EEG monitoring.

EXAMPLES

EEG with Copper Thread

Two individuals were fitted with the present device, one with a plastic disc electrodes and the other with a subdermal needle electrodes. The electrodes of both devices were connected to a wireless transmitter as described above with copper thread. The devices produced high quality and stable EEG data from all electrodes without artifacts. Impedances for both models were excellent, below 5-10 ohms, and were well-balanced. Each device was tested for 10 continuous minutes of recording. The subjects experienced no adverse effects.

Although the present invention has been described in considerable detail with reference to certain preferred embodiments, other embodiments are possible. The steps disclosed for the present methods, for example, are not intended to be limiting nor are they intended to indicate that each step is necessarily essential to the method, but instead are exemplary steps only. Therefore, the scope of the appended claims should not be limited to the description of preferred embodiments contained in this disclosure.

Recitation of value ranges herein is merely intended to serve as a shorthand method for referring individually to each separate value falling within the range. Unless otherwise indicated herein, each individual value is incorporated into the specification as if it were individually recited herein. All references cited herein are incorporated by reference in their entirety.

What is claimed is:

1. A transmitter adapted for use with an electroencephalography (EEG) device having a plurality of electrodes, wherein the transmitter consists of a device body comprising the following components:
   (a) a communications interface comprising an electrode interface that can be communicatively coupled to the plurality of electrodes of the EEG device;
   (b) a user interface on an outer surface of the device body, wherein the user interface includes a plurality of electrode impedance indicators, each indicator being associated with one of the plurality of electrodes when the electrode interface is communicatively coupled to the plurality of electrodes, wherein the indicators are disposed within a graphic image depicting a top plan view of a subject's head, the indicators being positioned relative to one another so that a position of a predetermined indicator in the graphic image correlates to a relative position of the electrode of the EEG device which is associated with the predetermined indicator; and
   (c) a processing circuit coupled with the communications interface and the user interface, the processing circuit adapted to:
      receive a respective electrical signal from each of the plurality of electrodes;
      measure an impedance associated with each electrode of the plurality of electrodes; and
      visually display via the electrode impedance indicator whether the impedance associated with each electrode is above or below a predetermined threshold.

2. The transmitter of claim 1, wherein the communications interface further comprises a wireless transceiver, and wherein the processing circuit is further adapted to simultaneously transmit via the wireless transceiver the impedance associated with each electrode and an electrical signal received by each electrode from a subject's brain.

3. The transmitter of claim 2, wherein the transmitter can wirelessly transmit the measured impedance values associated with each electrode via the wireless transceiver.

4. The transmitter of claim 1, wherein the electrode impedance indicators are light emitting diode (LED) lights.

5. The transmitter of claim 4, wherein the LED lights glow a first color when impedance levels for a respective electrode are below the predetermined threshold, and glow a second color when impedance levels for the respective electrode are above the predetermined threshold.

6. The transmitter of claim 1, wherein the predetermined threshold is 15 kilohms.

7. The transmitter of claim 1, wherein the transmitter further comprises an impedance excitation module for obtaining impedance measurements, wherein the impedance excitation module can send a DC or AC current to each of the electrodes.

8. The transmitter of claim 7, wherein the processing circuit measures voltage generated for each electrode from the current to determine an impedance value for each electrode with respect to a reference value.

9. The transmitter of claim 7, further comprising a test input button, wherein the impedance excitation module can be activated by the test input button.

10. The transmitter of claim 1, wherein the transmitter further comprises a programmable gain amplifier.

11. The transmitter of claim 1, wherein the processing circuit is adapted to send DC or AC current into each of the electrodes of the plurality of electrodes.

12. An electroencephalography (EEG) device comprising a processor, an amplifier, and a transmitter housed in a device body, the EEG device being adapted for use with a head strap having a plurality of electrodes, the EEG device further comprising:
 (a) a communications interface comprising an electrode interface that can be communicatively coupled to the plurality of electrodes;
 (b) a user interface on an outer surface of the device body, wherein the user interface includes a plurality of electrode impedance indicators, each indicator being associated with one of the plurality of electrodes when the electrode interface is communicatively coupled to the plurality of electrodes,
 wherein the indicators are disposed within a graphic image depicting a top plan view of a subject's head, the indicators being positioned relative to one another so that a position of a predetermined indicator in the graphic image correlates to a relative position of the electrode of the EEG device which is associated with the predetermined indicator, and
 wherein the electrode impedance indicators are light emitting diode (LED) lights that glow a first color when impedance levels for a respective electrode are below a predetermined threshold and glow a second color when impedance levels for the respective electrode are above the predetermined threshold; and
 (c) a storage medium in communication with the processor and comprising instructions for:
   receiving a respective electrical signal from each of the plurality of electrodes;
   measuring an impedance associated with each electrode of the plurality of electrodes; and
   visually displaying via the electrode impedance indicator whether the impedance associated with each electrode is above or below the predetermined threshold.

13. The EEG device of claim 12, further comprising a receiver.

14. The EEG device of claim 12, wherein the transmitter is a transceiver.

15. The EEG device of claim 12, wherein the transmitter sends wireless signals using WiFi transmission standards or Bluetooth transmission standards.

16. The EEG device of claim 12, further comprising a filter circuit coupled to the amplifier.

17. The EEG device of claim 12, further comprising an analog-to-digital converter circuit.

18. The EEG device of claim 12, wherein the storage medium comprises instructions for sending DC or AC current into each of the electrodes of the plurality of electrodes.

19. A transmitter adapted for use with an electroencephalography (EEG) device having a plurality of electrodes, wherein the transmitter consists of a device body comprising the following components:
 (a) a communications interface comprising an electrode interface that can be communicatively coupled to the plurality of electrodes of the EEG device;
 (b) a user interface on an outer surface of the device body, wherein the user interface includes a plurality of electrode impedance indicators, each indicator being associated with one of the plurality of electrodes when the electrode interface is communicatively coupled to the plurality of electrodes, wherein the indicators are disposed within a graphic image depicting a top plan view of a subject's head, the indicators being positioned relative to one another so that a position of a predetermined indicator in the graphic image correlates to a relative position of the electrode of the EEG device which is associated with the predetermined indicator; and
 (c) a processing circuit coupled with the communications interface and the user interface, the processing circuit adapted to:
   send DC or AC current into each of the electrodes of the plurality of electrodes;
   receive a respective electrical signal from each of the plurality of electrodes;
   measure an impedance associated with each electrode of the plurality of electrodes; and
   visually display via the electrode impedance indicator whether the impedance associated with each electrode is above or below a predetermined threshold.

* * * * *